United States Patent [19]

Miller

[11] Patent Number: 4,992,544
[45] Date of Patent: Feb. 12, 1991

[54] MONOCYCLIC BETA-LACTAMS AND PROCESS FOR THE PREPARATION THEREOF

[75] Inventor: Marvin J. Miller, South Bend, Ind.

[73] Assignee: University of Notre Dame du Lac, Notre Dame, Ind.

[21] Appl. No.: 890,600

[22] Filed: Jul. 25, 1986

Related U.S. Application Data

[63] Continuation of Ser. No. 612,986, May 23, 1984, abandoned, which is a continuation-in-part of Ser. No. 358,722, Mar. 16, 1982, abandoned.

[51] Int. Cl.$^5$ ............... C07D 205/085; C07D 205/08; C07D 205/09; C07D 417/12
[52] U.S. Cl. .................................................. 540/355
[58] Field of Search ......................................... 540/355

[56] References Cited

U.S. PATENT DOCUMENTS

| | | | |
|---|---|---|---|
| 4,107,304 | 8/1978 | Schrock et al. | 424/246 |
| 4,224,442 | 9/1980 | Cooper | 544/27 |
| 4,337,197 | 6/1982 | Gordon et al. | 544/355 |

FOREIGN PATENT DOCUMENTS

DE 3328047  2/1984  Fed. Rep. of Germany .

OTHER PUBLICATIONS

Woulfe, Tet. Letters, 25, 3293 (1984).
Atherton, Chem. Abs. 101, 6897.
Brewer et al., *Chem. Abs.* 101, 38265(g), 2-9-84.
Miller et al., J. Org. Chem. 47, 4828-33(1982).

*Primary Examiner*—Mark L. Berch
*Attorney, Agent, or Firm*—William B. Scanlon; Leroy Whitaker

[57] ABSTRACT

Monocyclic β-lactam compounds represented by the formula

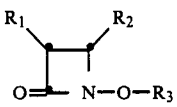

wherein $R_1$ is H, $NH_2$, acylamino, $C_1$–$C_4$ alkyl, etc.; $R_2$ is e.g. $C_1$–$C_4$ alkyl, hydroxyalkyl, aminoalkyl, carboxy, esterified carboxy, esterified carboxyalkyl, or carboxyalkyl; and $R_3$ is hydrogen, benzyl, substituted benzyl, pivaloyl, —$SO_3M$, or —P(C=O)(OM')$_2$; are obtained by the cyclization of an O-substituted hydroxamate of a β-substituted alkylcarboxylic acid. For example, α-ethylmalic acid monobenzyl ester is reacted with O-benzylhydroxylamine to form the O-benzylhydroxamate of the free carboxy group, and the hydroxamate is cyclized with diethyl diazodicarboxylate and triphenylphosphine to form the β-lactam of the above formula wherein $R_1$ is ethyl, $R_2$ is benzyloxycarbonyl and $R_3$ is benzyl. The β-lactam compounds are useful intermediates for preparing β-lactamase inhibitors and monocyclic β-lactam antibiotics and, when $R_3$ is —$SO_3M$ or —P(C=O)(OM')$_2$ the compounds and salts thereof are antibacterial agents.

16 Claims, No Drawings

MONOCYCLIC BETA-LACTAMS AND PROCESS FOR THE PREPARATION THEREOF

The invention described herein was made in the course of work under a grant or award from the Department of Health and Human Services.

CROSS-REFERENCE TO RELATED APPLICATION

This application is a continuation of application Ser. No. 612,986, filed May 23, 1984, which was a continuation-in-part of application Ser. No. 358,722, filed Mar. 16, 1982 abandoned.

BACKGROUND OF THE INVENTION

This invention relates to monocyclic β-lactam compounds and to processes for the preparation thereof. In particular, it relates to monocyclic β-lactam compounds which are useful in the preparation of β-lactam containing antibiotic compounds and β-lactamase inhibiting compounds and to monocyclic β-lactam antibiotics.

The class of β-lactam antibiotics includes the well-known penicillin and cephalosporin antibiotics. Recently, newer types of β-lactam antibiotics have been discovered. For example, thienamycin, Abers-Schonberg, et al., *J. Am. Chem. Soc.*, 100, 6491 (1978); nocardicin, H. Aoki, et al., 15th Interscience Conference on Antimicrobial Agents and Chemotherapy, Abstract no. 97, September 1975; clavulanic acid, U.S. Pat. No. 4,072,569; isoclavulanic acid, U.S. Pat. No. 4,297,345; and monolactam, Belg. Pat. No. 887,428; all contain the β-lactam ring characteristic of the penicillins and cephalosporin antibiotics.

Because of the high antibacterial activity and low toxicity generally exhibited by the β-lactam antibiotics, considerable research has been directed of late to the synthesis of new monocyclic β-lactams and to new methods for the preparation of β-lactams.

SUMMARY OF THE INVENTION

Monocyclic β-lactam compounds represented by the formula,

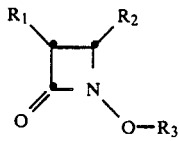

wherein $R_1$ and $R_2$ are substituents, e.g. $R_1$ is amino, acylamino, and $R_2$ is alkyl or substituted alkyl, e.g. carboxy, esterified carboxy or substituted alkyl, and $R_3$ is hydrogen, —SO$_3$M, —PO$_3$M$_2'$, or a group removable under reductive or hydrolytic conditions, are prepared by the intramolecular cyclization of a β-substituted monohydroxamate derivative of a monoester of an α,ω-dicarboxylic acid.

The compounds are useful as antibiotics and intermediates in the preparation of β-lactam antibiotics and β-lactamase inhibitors.

DETAILED DESCRIPTION

The β-lactam compounds of this invention are represented by the following formula 1

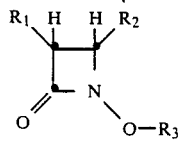

wherein $R_1$ is hydrogen, hydroxy, $C_1$-$C_4$ alkyl, substituted $C_1$-$C_4$ alkyl substituted by hydroxy, amino, protected amino, carboxy, protected carboxy, or halogen; $C_1$-$C_4$ alkoxy, $C_1$-$C_5$ alkanoyloxy, benzoyloxy, substituted benzoyloxy, azido, amino, protected amino, or a substituted amino group represented by the formula

wherein $R_1'$ is tri($C_1$-$C_4$ alkyl)silyl, $C_1$-$C_5$ alkanoyl, substituted $C_2$-$C_5$ alkanoyl substituted by halogen, cyano, or hydroxy; an arylacetyl or heteroarylacetyl group represented by the formula

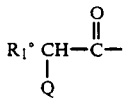

wherein $R_1°$ is thienyl, furyl, thiazolyl, oxazolyl, isoxazolyl, isothiazolyl, pyrazolyl, thiadiazolyl, oxadiazolyl, pyridyl, and said heterocyclic rings substituted by $C_1$-$C_4$ alkyl, amino, protected amino, or hydroxy; cyclohexadienyl, phenyl, or a substituted phenyl group represented by the formula

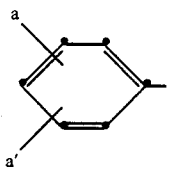

wherein a and a' independently are hydrogen, halogen, hydroxy, $C_1$-$C_4$ alkyl, $C_1$-$C_4$ alkoxy, amino, aminomethyl, methylsulfonylamino, hydroxymethyl, trifluoromethyl, carboxy, protected carboxy, carboxymethyl, or protected carboxymethyl;

Q is hydrogen, hydroxy, $C_1$-$C_4$ alkanoyloxy, carboxy, protected carboxy, sulfo(—SO$_3$H), amino, protected amino, or a substituted amino group represented by the formula

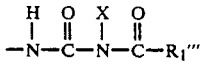

wherein x is hydrogen or $C_1$-$C_3$ alkyl; $R_1'''$ is furyl, thienyl, phenyl, halophenyl, nitrophenyl, styryl, halostyryl, nitrostyryl; or a group of the formula

wherein y is hydrogen or $C_1$-$C_3$ alkyl; $R_1''''$ is hydrogen, $C_1$-$C_4$ alkyl, benzyl, $C_2$-$C_5$ alkanoyl, or $C_1$-$C_3$ alkylsulfonyl; and when $R_1'''$ is —N(y)—$R_1''''$ x and y may be taken together to form a 5- or 6-membered ring represented by the formula

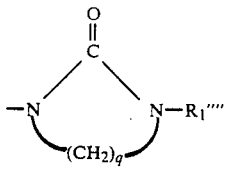

wherein $R_1''''$ has the same meanings as defined hereinabove and q is 2 or 3; or Q is a substituted amino group represented by the formula

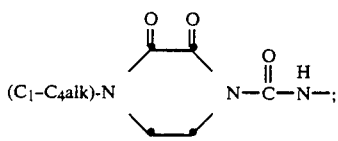

or $R_1'$ is an acyl group of the formula

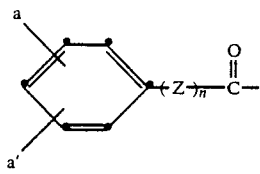

wherein a and a' have the same meanings as defined above, Z is O or S, and n is 0 or 1; or $R_1'$ is an oximino-substituted acyl group represented by the formula

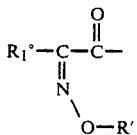

wherein $R_1°$ is as defined above, and R' is hydrogen, $C_1$-$C_4$ alkyl, or a carboxy-substituted alkyl or cycloalkyl group represented by the formula

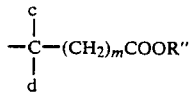

wherein m is 0–3, and c and d when taken separately are independently hydrogen or $C_1$-$C_3$ alkyl, and when taken together with the carbon atom to which they are bonded form a 3 to 6-membered carbocyclic ring; and wherein R'' is hydrogen, $C_1$-$C_4$ alkyl, or a carboxy-protecting ester forming group;

$R_1''$ is hydrogen, tri($C_1$-$C_4$ alkyl)silyl, or $R_1'$ and $R_1''$ when taken together with the nitrogen atom to which they are bonded form a diacyl group represented by the formula

wherein

Y is $C_1$-$C_3$ alkylene or o-phenylene;

$R_2$ is hydrogen, carboxy, $C_1$-$C_4$ alkoxycarbonyl, protected carboxy, formyl, $C_1$-$C_4$ alkyl, or $C_1$-$C_4$ alkyl substituted by hydroxy, halogen, carboxy, $C_1$-$C_4$ alkoxycarbonyl, protected carboxy, $C_1$-$C_4$ alkoxy, $C_1$-$C_4$ alkylthio, $C_1$-$C_5$ alkanoyloxy, $C_1$-$C_4$ alkylsulfonyloxy, phenylsulfonyloxy, tolylsulfonyloxy, halophenylsulfonyloxy, amino, protected amino, carboxy or protected carboxy-substituted $C_2$-$C_3$ alkanoyl, or $C_1$-$C_4$ alkylsulfonyloxy-substituted $C_2$-$C_3$ alkanoyl;

$R_3$ is hydrogen, $C_1$-$C_4$ alkyl, benzyl, methoxybenzyl, nitrobenzyl, diphenylmethyl, trityl, 2-methylsulfonylethyl, pivaloyl, or a group represented by the formula

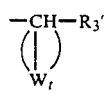

wherein W is hydrogen, methyl, phenyl, or mono- or dihydroxyphenyl; t is 0–4; and $R_3'$ is

wherein $R_3''$ is hydrogen, a carboxy-protecting group or an alkali or alkaline earth metal cation;

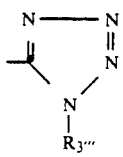

wherein $R_3'''$ is hydrogen or an alkali or alkaline earth metal cation;

—$SO_3M$,

—O—$SO_3M$,

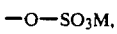

where in the above formula M and M' are hydrogen, an alkali or alkaline earth metal cation, or an ammonium or substituted ammonium cation; and M'' is $C_1$-$C_4$ lower alkyl, benzyl, or phenyl; provided that when $R_3'$ is —$COOR_3''$, $OSO_3M$, or

then t is other than O; and when t is greater than 1, only one of W can be other than hydrogen; and provided further than when $R_3$ is hydrogen, benzyl, methoxybenzyl, pivaloyl or —SO$_3$M and $R_1$ is amino, protected amino, or substituted amino, then $R_2$ is other than hydrogen or $C_1$-$C_4$ alkyl.

As used in the above description of the compounds of formula 1, "$C_1$-$C_4$ alkyl" refers to the straight and branched chain hydrocarbon radicals such as methyl, ethyl, n-propyl, isopropyl, n-butyl, secbutyl, t-butyl, and the like; "substituted $C_1$-$C_4$ alkyl" refers to the —$C_1$-$C_4$ alkyl radicals substituted by hydroxy, amino, carboxy, or halogen such as hydroxymethyl, 1-hydroxyethyl, 2-hydroxyethyl, 2-hydroxypropyl, 4-hydroxybutyl, aminomethyl, 2-aminoethyl, 3-aminopropyl, 2-aminopropyl, 2-carboxyethyl, 3-carboxypropyl, 3-carboxybutyl, chloromethyl, bromomethyl, 2-chloromethyl, 2-fluoroethyl, 3-chloropropyl, 4-bromobutyl, and like substituted $C_1$-$C_4$ alkyl groups. The term "$C_1$-$C_4$ alkoxy" refers to methoxy, ethoxy, n-propoxy, isopropoxy, t-butoxy, and the like. "Halogen" refers to fluoro, chloro, or bromo. "$C_1$-$C_5$ alkanoyloxyp" refers to formyloxy, acetoxy, propionyoxy, butyryoxy, valeryloxy, and the like. "Benzoyloxy" and "substituted benzoyloxy" refers to the group represented by the formula

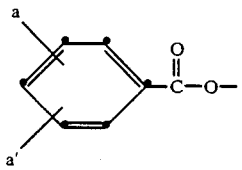

wherein a and a' have the same meanings as defined hereinabove. "$C_1$-$C_5$ alkanoyl" refers to formyl, acetyl, propionyl, butyryl, isobutyryl, pivalyl, and the like. "Substituted $C_2$-$C_5$ alkanoyl" refers to the previously mentioned alkanoyl groups substituted by halogen, cyano or hydroxy, for example chloroacetyl, bromoacetyl, cyanoacetyl, chloropropionyl, bromobutyryl, 3-cyanopropionyl, hydroxybutyryl, and the like.

The term "tri($C_1$-$C_4$ alkyl)silyl" refers to mixed and unmixed alkyl silyl groups such as trimethylsilyl, triethylsilyl, tri-n-butylsilyl, t-butyldimethylsilyl, t-butyldiethylsilyl, and like groups.

The term "protected amino" refers to the substituted amino groups wherein the substituent is a readily removable blocking group commonly employed in the β-lactam art for the temporary protection of basic amino groups. The protecting substituent group is functional only, serving to prevent the basic amino group from interfering with reactions carried out at other sites in the molecule. For example, an amino group is desirably protected during the acylation of a hydroxy group elsewhere in the molecule. Such protection prevents the competitive N-acylation of an unprotected amino group. Amino protecting groups are wellknown in the art and a few examples suffice to illustrate the types that can be employed herein. Examples of such groups are those forming carbamic esters with the amino, e.g. t-butyloxycarbonyl, 2,2,2-trichloroethoxycarbonvl, cyclopentyloxycarbonyl, benzyloxycarbonyl, p-nitrobenzyloxycarbonyl; those forming enamines of the amino group, such as for example, methyl acetoacetate, ethyl acetoacetate, acetoacetone, and the like; and in addition, other known amino-protecting groups such as trityl (triphenylmethyl); haloacyl groups such as mono or dichloroacetyl; and tricarbylsilyl groups, e.g. butyldimethylsilyl and phenyldimethylsilyl.

As used herein the term "protected carboxy" refers to the esterified carboxylic acid function wherein the ester moiety is one recognized in the art as useful for the temporary protection or blocking of the acidic carboxy group. Such esters include for example the alkyl and substituted alkyl esters such as t-butyl, 2,2,2-trichloroethyl, 2,2,2-tribromoethyl, 2-iodoethyl, alkyl and substituted alkyl esters such as 3-methylbutene-3-yl, and 3-ethylpentene-3-yl; the benzyl and substituted benzyl esters such as p-nitrobenzyl, p-methoxybenzyl, p-methylbenzyl, diphenylmethyl, and 4-methoxydiphenylmethyl; the tricarbylsilyl esters such as trimethylsilyl, triethylsilyl, t-butyldimethylsilyl, phenyldimethylsilyl, and like esters.

In the compounds represented by the formula 1 the term $R_1$ can be a substituted amino group as defined. Examples of such acyl groups include those represented by the formula ($R_1°$ is phenyl or substituted phenyl)

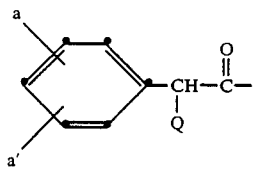

wherein Q is hydrogen, for example phenylacetyl, 4-hydroxyphenylacetyl, 3-hydroxyphenylacetyl, 4-hydroxy-3-chlorophenylacetyl, 4-chlorophenylacetyl, 3,4-dichlorophenylacetyl, 2-fluorophenylacetyl, 4-methylphenylacetyl, 3-ethylphenylacetyl, 3-chloro-4-methylphenylacetyl, 4-isopropylphenylacetyl, 4-methoxyphenylacetyl, 4-t-butoxyphenylacetyl, 3-isopropoxyphenylacetyl, 3-methoxy-4-hydroxyphenylacetyl, 3-trifluoromethylphenylacetyl, 4-trifluoromethylphenylacetyl, 3-aminophenylacetyl, 2-aminophenylacetyl, 2-aminomethylphenylacetyl, 3-(methylsulfonylamino)phenylacetyl, 2-hydroxymethylphenylacetyl, 4-hydroxymethylphenylacetyl, 4-carboxymethylphenylacetyl, 4-carboxyphenylacetyl, 3-carboxyphenylacetyl, 4-ethoxycarbonylphenylacetyl, and like phenylacetyl groups.

When Q is hydroxy or $C_1$-$C_4$ alkanoyloxy and $R_1°$ is phenyl or substituted phenyl, illustrative examples of such acyl groups are α-hydroxyphenylacetyl (mandeloyl), α-formyloxyphenylacetyl, α-acetoxyphenylacetyl, 4-methylmandeloyl, 3,4-dichloromandeloyl, 3-bromomandeloyl, 4-hydroxymandeloyl, 3-trifluoromethylmandeloyl, 2-hydroxymethylmandeloyl, 2-aminomethylmandeloyl, 3-carboxymandeloyl, 4-methoxycarbonylmethylmandeloyl, 3-aminomandeloyl, and like substituted acyl groups.

Examples of acyl groups when $R_1°$ is phenyl or substituted phenyl and Q is amino or protected amino are phenylglycyl, 4-hydroxyphenylglycyl, 3-hydroxyphenylglycyl, 3-methylphenylglycyl, 4-ethylphenylglycyl, 4-chlorophenylglycyl, 3-methyl-4-chlorophenylglycyl, 4-hydroxy-3,5-dichlorophenylglycyl, 3-aminomethylphenylglycyl, 3-(methylsulfonylamino)phenylglycyl, 4-hydroxymethylphenylglycyl, 4-carboxymethylphenylglycyl, 3-carboxyphenylglycyl, 4-trifluoromethylphenylglycyl, and the like, and N-t-butyloxycarbonyl protected and enamine (formed with ethylacetoacetate) protected derivatives of the above phenylglycyl groups.

When $R_1°$ is phenyl or substituted phenyl and Q is carboxy, esterified carboxy, or sulfo, examples of acyl groups represented are α-carboxyphenylacetyl, α-sulfophenylacetyl, α-carboxy-4-hydroxyphenylacetyl, α-carboxy-4-methoxyphenylacetyl, α-ethoxycarbonylphenylacetyl, α-carboxy-3-trifluoromethylphenylacetyl, α-carboxy-4-aminomethylphenylacetyl, α-carboxy-4-methylphenylacetyl, α-carboxy-3-bromophenylacetyl, α-carboxy-4-fluorophenylacetyl, and like acyl groups.

When in the formula 1, $R_1°$ is phenyl or substituted phenyl and Q is a substituted amino group represented by the formula

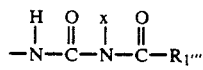

the group represented are (1) acylureido groups such as 3-benzoylureido, 3-benzoyl-3-methylureido, 3-furoylureido, 3-thenoylureido, 3-(2-chlorobenzoyl)ureido, 3-(4-nitrobenzoyl)ureido, 3-cinnamoylureido, 3-(2-chlorocinnamoyl)ureido, 3-(2,4-dichlorobenzoyl)ureido, 3-(3-bromocinnamoyl)ureido, 3-(2-chlorobenzoyl)-3-methylureido, 3-(2-fluorobenzoyl)ureido, and like acylureido groups; and when $R_1'''$ is a group of the formula

(2) carbamoylureido groups as, for example, 3-(carbamoyl)ureido, 3-(N-methylcarbamoyl)ureido, 3-(N-ethylcarbamoyl)ureido, 3-(N-benzylcarbamoyl)ureido, 3-(N-methylcarbamoyl)-3-methylureido, 3-(N-acetylcarbamoyl)-3-methylureido, 3-(N-methylsulfonylcarbamoyl)-3-methylureido, and like groups; and when x and y are taken together to form a 5- or 6-membered ring, (3) cyclic ureido groups such as, for example, imidazolidin-2-ones represented by the formula (q=2)

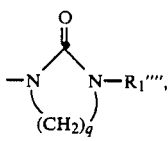

imidazolidin-2-one-1-yl, 3-imidazolidin-2-one-1-yl, 3-ethylimidazolidin-2-one-1-yl, 3-acetylimidazolidin-2-one-1-yl, 3-(methylsulfonyl)imidazolidin-2-one-1-yl, and the like; and the hexahydropyrimidin-2-ones (q=3) such as hexahydropyrimidin-2-one-1-yl, 3-ethylhexahydropyrimidin-2-one-1-yl, 3-acetylhexahydropyrimidin-2-one-1-yl, 3-(methylsulfonyl)hexahydropyrimidin-2-one-1-yl; and like ureido groups.

When $R_1°$ is a heteroaryl group representative acyl groups are for example, 2-thienylacetyl, 3-thienylacetyl, α-amino-2-thienylacetyl, α-carboxy-2-thienylacetyl, α-hydroxy-2-thienylacetyl, α-sulfo-2-thienylacetyl, 2-furylacetyl, α-amino-2-furylacetyl, α-carboxy-2-furylacetyl, thiazol-4-ylacetyl, 2-aminothiazol-4-ylacetyl, oxazol-4-ylacetyl, 2-methyloxazol-4-ylacetyl, isoxazol-4-ylacetyl, isoxazol-3-ylacetyl, 5-methylisoxazol-4-ylacetyl, α-amino-(isoxazol-3-yl)acetyl, isothiazol-4-ylacetyl, 5-pyrazolylacetyl, 5-methyl-1,3,4-thiadiazol-2-ylacetyl, α-amino(5-methyl-1,3,4-thiadiazol-2-ylacetyl, 5-methyl-1,3,4-oxadiazol2-ylacetyl, α-sulfo-(5-methyl-1,3,4-oxadiazol-2-yl)acetyl, 1,2,4-thiadiazol-3-ylacetyl, pyridin-2-ylacetyl, 2-aminopyridin-5-ylacetyl, and like acyl groups.

Examples of acyl groups $R_1'$ (formula 1) represented by the formula

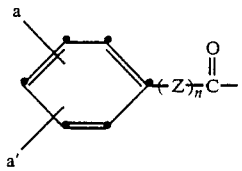

when n is 0 are benzoyl, 4-methylbenzoyl, 3-chlorobenzoyl, 4-carboxybenzoyl, 3-aminobenzoyl, 4-trifluoromethylbenzoyl, 2,6-dimethoxybenzoyl, and the like; and when n is 1 and Z is O, phenoxyacetyl, 4-chlorophenoxyacetyl, 3-bromophenoxyacetyl, 3-aminomethylphenoxyacetyl, 2-hydroxymethylphenoxyacetyl, 4-trifluoromethylphenoxyacetyl, 2-aminophenoxyacetyl and like substituted phenoxyacetyl groups; and when n is 1 and Z is S, examples of such acyl groups are phenylmercaptoacetyl, 4-chlorophenylmercaptoacetyl, 3,5-dichlorophenylmercaptoacetyl, 4-fluorophenylmercaptoacetyl, 2,4-dichlorophenylmercaptoacetyl, 3-aminophenylmercaptoacetyl, 4-aminomethylphenylmercaptoacetyl, 2-carboxyphenylmercaptoacetyl, 4-trifluoromethylphenylmercaptoacetyl, 3,4-dimethoxyphenylmercaptoacetyl, 4-methylphenylmercaptoacetyl, and like acyl groups.

Illustrative examples of acyl groups ($R_1'$) represented by the formula

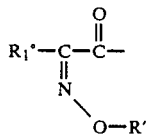

wherein R' is hydrogen or $C_1$-$C_4$ alkyl, are 2-furyl-2-methoxyiminoacetyl, 2-thienyl-2-methoxyiminoacetyl, 2-(2-aminothiazol-4-yl)-2-methoxyiminoacetyl, (2-methoxyimino)-phenylacetyl, 2-(isopropoxyimino)-phenylacetyl, 2-(isoxazol-4-yl)-2-methoxyiminoacetyl, 2-(5-methyl-1,3,4-thiadiazol-2-yl)-2-methoxyiminoacetyl, 2-(2-aminooxazol-4-yl)-2-hydroxyiminoacetyl, 2-(t-butoxyimino)-phenylacetyl, and the like.

When in the above formula R' is a carboxysubstituted alkyl or cycloalkyl group represented by the formula

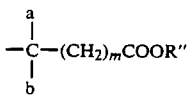

examples of such groups are carboxymethyl, 2-carboxyethyl, 3-carboxypropyl, 4-carboxybutyl, 1-carboxyeth-1-yl, 2-carboxyprop-2-yl, 3-carboxybut-2-yl, 5-carboxy-2-methylpent-2-yl, 4-carboxy-2-ethylbut-2-yl, 1-carboxycycloprop-1-yl, 1-carboxycyclobut-1-yl, 1-carboxycyclopent-1-yl, 1-carboxycyclohex-1-yl, 1-(carboxymethyl)cyclopent-1-yl, 1-(3-carboxypropyl)cyclohex-1-yl, and the $C_1$-$C_4$ alkyl esters of such carboxy-substituted alkyl and cycloalkyl groups.

Illustrative of the carboxy-substituted alkyl and carboxy-substituted cycloalkyl bearing oximino acyl groups are 2-(2-aminothiazol-4-yl)-2-ethoxycarbonylmethoxyiminoacetyl, 2-(2-aminothiazol-4-yl)-2-carboxymethoxyiminoacetyl, 2-(2-aminothiazol-4-yl)-2-(2-carboxyprop-2-yl)oxyiminoacetyl, 2-(2-hydroxythiazol-4-yl)-2-(2-carboxyprop-2-yl)oxyiminoacetyl, 2-(2-aminothiazol-4-yl)-2-(1-carboxycyclobut-1-yl)oxyiminoacetyl, 2-(2-furyl)-2-(2-carboxyprop-2-yl)oxyiminoacetyl, 2-phenyl-2-(1-carboxycyclopent-1-yl)oxyiminoacetyl, 2-phenyl-2-(3-carboxyprop-1-yl)oxyiminoacetyl, 2-(2-thienyl)-2-(1-carboxybut-1-yl)oxyiminoacetyl, 2-(5-methyl-1,3,4-thiadiazol-2-yl-2-ethoxycarbonylmethoxyiminoacetyl, 2-(5-amino-1,3,4-thiadiazol-2-yl)-2-(2-carboxyethoxyimino)acetyl, 2-(5-amino-1,3,4-oxadiazol-2-yl)-2-(2-carboxybut-2-yl)oxyiminoacetyl, 2-(5-aminoisothiazol-3-yl)-2-(2-carboxyprop-2-yl)oxyiminoacetyl, 2-(5-aminoisoxazol-3-yl)-2-carboxymethoxyiminoacetyl, 2-(1,4-cyclohexadien-1-yl)-2-(2-carboxyprop-2yl)oxyiminoacetyl, 2-(4-hydroxyphenyl)-2-hydroxyiminoacetyl, 2-(6-aminopyridin-2-yl)-2-(2-carboxyhex-2yl)oxyiminoacetyl, and like oximino acyl groups.

The following examples illustrate the defined groups, $R_2$, representing the substituent in the 4-position of the azetidin-2-one ring. The term $C_1$–$C_4$ alkyl substituted by hydroxy represents for example, hydroxymethyl, 1-hydroxyethyl, 2-hydroxyethyl, 2-hydroxypropyl, and the like; $C_1$–$C_4$ alkyl substituted by halogen refers to bromomethyl, iodomethyl, 2-chloroethyl, 3-chloropropyl, and the like; $C_1$–$C_4$ alkyl substituted by carboxy, protected carboxy, or $C_1$–$C_4$ alkoxycarbonyl refers to such groups as 2-carboxyethyl, carboxymethyl, 2-ethoxycarbonylethyl, 2-(t-butyloxycarbonyl)ethyl, 3-methoxycarbonylpropyl, p-nitrobenzyloxycarbonylmethyl, 2-benzyloxycarbonylmethyl, 3-(t-butyloxycarbonyl)butyl, and the like; $C_1$–$C_4$ alkyl substituted by $C_1$–$C_4$ alkoxy or $C_1$–$C_4$ alkylthio refers to radicals such as methoxymethyl, 2-ethoxyethyl, 1-methoxyethyl, 3-t-butyloxypropyl, 2-isopropoxyethyl, methylthiomethyl, 2-ethylthioethyl, n-butylthiomethyl, 2-n-propylthioethyl, and the like; $C_1$–$C_4$ alkyl substituted by $C_1$–$C_4$ alkylsulfonyloxy, phenylsulfonyloxy, tolylsulfonyloxy, or halophenylsulfonyloxy refers to groups such as methylsulfonyloxymethyl, 2-methylsulfonyloxyethyl, ethylsulfonyloxymethyl, 2-n-propylsulfonyloxyethyl, p-toluenesulfonyloxymethyl, 2-benzenesulfonyloxyethyl, p-chlorobenzenesulfonyloxymethyl, 3-p-toluenesulfonyloxypropyl, 1-(p-bromobenzenesulfonyloxy)ethyl, and the like; $C_1$–$C_4$ alkyl substituted by amino or protected amino refers to groups such as aminomethyl, 2-aminoethyl, 3-aminopropyl, 1-aminoethyl, 4-aminobutyl, 3-aminobutyl, t-butyloxycarbonylaminomethyl, 2-benzyloxycarbonylaminoethyl, 1-p-nitrobenzyloxycarbonylaminoethyl, 3-tritylaminopropyl, and the like; $C_1$–$C_4$ alkyl substituted by carboxy or protected carboxysubstituted $C_2$–$C_3$ alkanoyl refers to radicals represented by the formulas —CH$_2$—C(O)—CH$_2$COOC$_2$H$_5$, —CH$_2$—CH$_2$—C(O)—CH$_2$COOCH$_2\phi$, —CH$_2$—C(O)—CH$_2$—CH$_2$COO t-butyl,

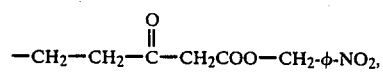

—CH$_2$—C(O)—(CH$_2$)$_3$COOH, —CH$_2$—CH$_2$—C(O)—(CH$_2$)$_2$COOH, and like keto acid and keto ester radicals; and $C_1$–$C_4$ alkyl substituted by $C_1$–$C_4$ alkylsulfonyloxy-substituted $C_2$–$C_3$ alkanoyl refers to radicals represented by the formulas —CH$_2$—C(O)—CH$_2$CH$_2$—OSO$_2$CH$_3$, —CH$_2$—C(O)—CH$_2$CH$_2$—O—SO$_2$C$_2$H$_5$, —CH$_2$—CH$_2$—C(O)—CH$_2$—O—SO$_2$CH$_3$, and the like.

When in the formula 1 $R_1$ is a disubstituted group,

and $R_1'$ and $R_1''$ are taken together to form a diacylamino group, $R_1$ is exemplified by phthalimido, chlorophthalimido, and succinimido.

Disubstituted amino radicals $(R_1')(R_1'')$N—, wherein $R_1'$ and $R_1''$ are tri($C_1$–$C_4$ alkyl)silyl, are exemplified by bis-(trimethylsilyl)amino, bis-(triethylsilyl)amino, bis-(t-butyldimethylsilyl)amino, and like radicals.

Illustrative groups of the formula 1 wherein $R_3$ is a group of the formula

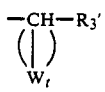

and $R_3'$ is —COOR$_3''$ are carboxymethyl, 2-carboxyethyl, 3-carboxypropyl, 4-carboxybutyl, and such groups in the sodium and potassium salt forms, carboxybehzyl, 2-carboxy-1-phenylethyl, 3-carboxy-2-phenylpropyl, methoxycarbonylmethyl, ethoxycarbonylmethyl, t-butyloxycarbonylmethyl, benzyloxycarbonylmethyl, 2-(diphenylmethoxycarbonyl)methyl, 2-(trimethylsilylethoxycarbonyl)methyl, 2-(p-nitrobenzyloxycarbonyl)ethyl, and like carboxy-substituted alkyl groups. When $R_3'$ is the 5-substituted tetrazole group, examples of such $R_3$ groups include 1H-tetrazole-5-yl, 1H-tetrazole-5-ylmethyl, 2-(1H-tetrazole-5-yl)ethyl, 3-(1H-tetrazole-5-yl)propyl, the 1H-tetrazole-5-yl-(4-hydroxybenzyl) group of the formula,

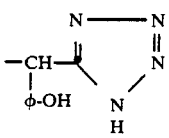

and like groups in the sodium or potassium salt forms of the tetrazole. When $R_3'$ is a group of the formula —SO$_3$M, representative sulfonic acids and salts thereof are illustrated by —SO$_3$Na, —CH$_2$SO$_3$Na, —CH$_2$—CH$_2$—SO$_3$H, —(CH$_2$)$_3$SO$_3$Na, —CH(C$_6$H$_5$)SO$_3$Na, —CH$_2$CH(C$_6$H$_5$)SO$_3$K, and —CH(C$_6$H$_4$OH)CH$_2$SO$_3$Na. When $R_3'$ is —O—SO$_3$M, examples of $R_3$ groups are —CH$_2$CH$_2$—OSO$_3$Na, —CH(C$_6$H$_5$)—CH$_2$O—SO$_3$H, CH—(CH$_3$)—OSO$_3$K, and —CH(CH$_3$)—CH$_2$—OSO$_3$Na. When $R_3'$ is the group —$\overset{O}{\underset{\|}{P}}$(OM')$_2$, examples of $R_3$ are —$\overset{O}{\underset{\|}{P}}$(OK)$_2$,

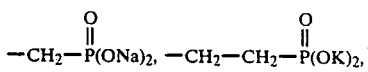

and —CH(CH$_3$)—$\overset{O}{\underset{\|}{P}}$(OK)$_2$,

-continued while when R₃' is the group $-O-\overset{\overset{O}{\|}}{P}(OM')(OM'')$, examples of R₃ are $-CH_2-O-\overset{\overset{O}{\|}}{P}(OK)_2$, $-CH_2-O-\overset{\overset{O}{\|}}{P}(OK)(OCH_3)$, $-CH_2-CH_2-O-\overset{\overset{O}{\|}}{P}-(OEt)(OH)$, $-CH_2-O-\overset{\overset{O}{\|}}{P}(OK)(OCH_2C_6H_5)$, and like groups.

In the above formulas M⁺ can be an alkali metal cation such as lithium, sodium or potassium cation, an alkaline metal cation such as calcium cation, or ammonium or substituted ammonium cation such as $C_1$–$C_4$ alkylammonium, di($C_1$–$C_4$ alkyl)ammonium, di(-substituted $C_1$–$C_4$ alkyl)ammonium, dicycloalkylammonium, for example, methylammonium, t-butylammonium, n-butylammonium, dimethylammonium, diethylammonium, cyclohexylammonium, dicyclohexylammonium, di-(2-hydroxyethyl)ammonium, di-(3-hydroxypropyl)ammonium, and like ammonium cations.

It will be appreciated that the salt form of the phosphate ester of the above formula may be formed with a diammonium cation such as is formed with a diamine for example, 1,3-diaminopropane or 1,4-diaminobutane. Likewise, the divalent calcium cation can be the counter ion for both of the phosphate anions. Also, the divalent Ca⁺⁺ cation serves as the counterion for two molecules of sulfate ester in anionic form.

The monocyclic β-lactam compounds of this invention (formula 1) are formally named herein as substituted azetidin-2-ones. The 4-membered β-lactam ring is essentially planar while the two hydrogen atoms in the 3- and 4-positions of a 3,4-disubstituted azetidinone can be either cis or trans as described hereinafter. The compounds of the invention are structurally characterized by an N-oxy group ($-O-R_3$) in the 1-position. The N-oxy group is either the N-hydroxy group ($R_3$=H) or the N-substituted hydroxy group ($R_3$ is other than H) e.g. benzyl, pivaloyl, $-SO_3-M^+$ or $-P(=O)(OM')_2$. This structural characteristic derives from the unique method by which the compounds of the invention are prepared.

Examples of azetidin-2-one compounds provided by this invention (formula 1) are described in the following Table I.

TABLE I

Substituted 1-Oxyazetidin-2-ones

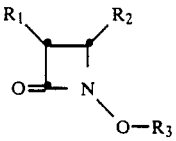

1

| R₁ | R₂ | R₃ |
|---|---|---|
| H | —COOCH₃ | methyl |
| H | —COOCH₂φ | t-butyl |
| Cl | —CH₂—O—SO₂CH₃ | pivaloyl |
| H | —COOH | pivaloyl |
| H | —CH₂OH | pivaloyl |
| H | —CH₂NH₂ | benzyl |
| H | —CHO | benzyl |
| H | —CH₂I | benzyl |
| H | —CH₂CH₂COOC₂H₅ | benzyl |
| H | —CH₂CH₂COOH | pivaloyl |
| H | —CH₂I | pivaloyl |
| OH | —CH₂COOCH₃ | pivaloyl |
| OH | —CHO | benzyl |
| OH | COOCH₂φ | t-butyl |
| OH | —CH₂CH₂I | t-butyl |
| OCH₃ | —COOCH₃ | benzyl |
| O-t-butyl | —COOH | benzyl |
| H | COOH | trityl |
| —CH(OH)—CH₃ | —COOCH₂φ | pivaloyl |
| —CH(OH)—CH₃ | —COOCH₂φ | trityl |
| —C₂H₅ | COOH | trityl |
| —OCOCH₃ | —COO-t-butyl | t-butyl |
| —OCOφ | —CH₂CH₃ | benzyl |
| t-BOCNH— | COOCH₃ | trityl |
| NH₂ | COOH | H |
| NH₂ | COOH | benzyl |
| NH₂ | —CH₂COOCH₂φ | benzyl |
| NH₂ | —C₃H₇ | H |
| CH₃CONH— | COOCH₃ | t-butyl |
| NCCH₂CONH— | COOC₂H₅ | benzyl |
| φ-CH₂CONH— | COOC₂H₅ | H |
| φ-O—CH₂CONH— | COOH | pivaloyl |
| φ-S—CH₂CONH— | —CH₂OH₂Br | t-butyl |
| 2-thienylacetamido | —CH₂OH | benzyl |
| 2-furylacetamido | —CH₂CH₂OH | benzyl |
| phthalimido | CH₃ | C₂H₅ |
| φ-CH(NH₂)CONH— | H | H |
| φ-CH(NH₂)CONH— | C₃H₇ | H |

TABLE I-continued

Substituted 1-Oxyazetidin-2-ones

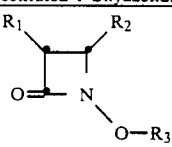

| R₁ | R₂ | R₃ |
|---|---|---|
| φ-CH(NH₂)CONH— | —CH₂OH | benzyl |
| φ-CH(NH₂)CONH— | —CH₂CH₂COOCH₂φ | benzyl |
| φ-CH(COOH)CONH— | CH₃ | pivaloyl |
| φ-CH(COOH)CONH— | —CH₂CH₂COOH | pivaloyl |
| φ-CH(COOH)CONH— | H | H |
| φ-CH(OH)CONH— | —COO t-butyl | t-butyl |
| φ-CH(OH)CONH— | —COOH | t-butyl |
| φ-CH(OH)CONH— | —CH₂OCH₃ | t-butyl |
| φ-CH(OH)CONH— | —C₃H₇ | pivaloyl |
| φ-C(O)NH— | COOCH₃ | pivaloyl |
| p-toluamido | COOCH₃ | pivaloyl |
| p-chlorobenzamido | COOCH₃ | pivaloyl |
| φ-C(=N—OCH₃)—C(O)NH— | CHO | H |
| φ-C(=N—OCH₃)—C(O)NH— | —CH₂OCOCH₃ | H |
| φ-C(=N—OCH₃)—C(O)NH— | —CH₂CH₂OH | benzyl |
| φ-C(=N—OCH₃)—C(O)NH— | —CH₂NH₂ | benzyl |
| 2-(2-aminothiazol-4-yl)-2-methoxyiminoacetamido | COOH | benzyl |
| 2-(2-aminothiazol-4-yl)-2-methoxyiminoacetamido | COOCH₂φ | pivaloyl |
| 2-(2-aminothiazol-4-yl)-2-methoxyiminoacetamido | —CH₂CH₂Cl | —CH₂—COOCH₃ |
| 2-(2-aminothiazol-4-yl)-2-methoxyiminoacetamido | —CH₂O—SO₂CH₃ | H |
| —N₃ | COOCH₃ | benzyl |
| ClCH₂CH₂— | COOCH₃ | benzyl |
| t-butyloxy | COO t-butyl | t-butyl |
| t-butyloxycarbamido | —CH₂CH₂OH | pivaloyl |
| C₂H₅ | COOCH₃ | benzyl |
| 2-(2-aminothiazol-4-yl)-2-aminoacetamido | COOC₂H₅ | H |
| (CH₃)₃COC(O)NH— | —CH₂—CH₂—CO₂CH₃ | benzyl |
| φ-CH₂—O—C(O)NH— | —CH₂—CH₂COCH₂CO₂CH₂- -NO₂ | t-butyl |
| φ-CH(NH₂)CO— | —CH₂—CH₂COCH₂CO₂CH₂-φ | t-butyl |
| NH₂.HCl | —COOH | —SO₃—Na⁺ |
| NH₂.HCl | —COOCH₂φ | —SO₃—K⁺ |
| NH₂.HCl | —COOCH₂φ | —PO₃—2Na⁺ |
| NH₂.HCl | —COOC₂H₅ | —PO₃—2K⁺ |
| NH₂.HCl | —CH₂CH₂OH | —PO₃—2K⁺ |
| φ-CH₂CONH— | —C₂H₅ | —SO₃⁻ K⁺ |
| φ-CH₂CONH— | —COOH | |
| φ-CH₂CONH— | —CH₂Cl | —SO₃⁻ K⁺ |
| φ-O—CH₂—CONH— | —COOCH₃ | —SO₃⁻ K⁺ |
| φ-CONH— | —COOCH₃ | —SO₃⁻ K⁺ |
| CH₃- -CONH— | —CH₂—COOC₂H₅ | —SO₃⁻ K⁺ |
| φ-CH(NH₂)CONH— | COOH | —SO₃⁻ K⁺ |
| φ-CH(NH₂)CONH— | —C₃H₇ | —SO₃⁻ K⁺ |
| φ-CH(OH)CONH— | —C₃H₇ | —SO₃⁻ K⁺ |
| φ-CH(OH)CONH— | COONa | —SO₃⁻ K⁺ |
| φ-CH(OH)CONH— | —CH₂CH₂OH | —SO₃⁻ K⁺ |
| φ-CH(COOH)CONH— | —CHO | —SO₃⁻ K⁺ |
| 2-(2-aminothiazol-4-yl)-2-methoxyiminoacetamido | COOCH₂φ | —SO₃⁻ K⁺ |
| | —CH₂—C(=O)—CH₂—COOC₂H₅ | —SO₃⁻ K⁺ |
| 2-(2-aminothiazol-4-yl)-2-methoxyiminoacetamido | —CH₂OH | —SO₃⁻ K⁺ |
| 2-(2-aminothiazol-4-yl)-2-methoxyiminoacetamido | —CH₂I | —SO₃⁻ K⁺ |
| 2-(2-aminothiazol-4-yl)-2-methoxyiminoacetamido | —CH₂I | —PO₃=2Na⁺ |
| 2-(2-aminothiazol-4-yl)-2-methoxyiminoacetamido | —COOK | —PO₃=2K⁺ |
| 2-(2-aminothiazol-4-yl)-2-methoxyiminoacetamido | —COONH₃ | —PO₃=2NH₃ |
| | —COO-t-butyl | —PO₃=2NH₃ |
| H₂N.HCl | COOH | —PO₃=2K⁺ |
| φ-CH₂CONH— | COOH | —PO₃=2K⁺ |
| p-toluamido- | C₂H₅ | —PO₃=2K⁺ |
| φ-O—CH₂—CONH— | —CH₂CH₂OH | —PO₃=2K⁺ |
| φ-O—CH₂—CONH— | —CH₂—CHO | —PO₃=2K⁺ |
| φ-CH(NH₂)CONH— | —CH₂—C(=O)—CH₂COOCH₂φ | —PO₃=2K⁺ |
| φ-CH(OH)CONH— | —CH₂CH₂COOH | —PO₃=2K⁺ |
| 2-(2-aminothiazol-4-yl)-2-methoxyimino-acetamido | COOH | —CH₂COOK |
| 2-(2-aminothiazol-4-yl)-2-methoxyimino-acetamido | H | —CH₂COONa |
| 2-(2-aminothiazol-4-yl)-2-methoxyimino-acetamido | CH₃ | —CH₂COONa |

TABLE I-continued

Substituted 1-Oxyazetidin-2-ones

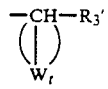

| R$_1$ | R$_2$ | R$_3$ |
|---|---|---|
| 2-(2-aminothiazol-4-yl)-2-methoxyimino-acetamido | COOH | —CH$_2$—SO$_3$K |
| 2-(2-aminothiazol-4-yl)-2-methoxyimino-acetamido | CH$_3$ | —CH$_2$—SO$_3$K |
| 2-(2-aminothiazol-4-yl)-2-methoxyimino-acetamido | —CH$_2$COOH | —CH$_2$COOH |
| 2-(2-aminothiazol-4-yl)-2-methoxyimino-acetamido | —CH$_2$COOH | —CH$_2$CH$_2$—SO$_3$K |
| 2-(2-aminothiazol-4-yl)-2-methoxyimino-acetamido | CH$_2$OH | —CH$_2$—CH$_2$COONa |
| 2-(2-aminothiazol-4-yl)-2-methoxyimino-acetamido | CH$_2$COOC$_2$H$_5$ | —CH$_2$—PO$_3$2K |
| 2-(2-aminothiazol-4-yl)-2-methoxyimino-acetamido | COOC$_2$H$_5$ | —CH$_2$CH$_2$—OPO$_3$2K |
| NH$_2$.HCl | COOH | —CH$_2$COONa |
| NH$_2$.HCl | COOH | —CH$_2$SO$_3$K |
| 2,6-dimethoxybenzamido | H | —CH$_2$—CH$_2$COOK |
| 2-aminothiazol-4-yl-acetamido | H | —CH$_2$COONa |
| 2-aminothiazol-4-yl-acetamido | CH$_3$ | —CH$_2$COONa |
| 2-aminothiazol-4-yl-acetamido | COONa | —CH$_2$COONa |
| 2-aminothiazol-4-yl-acetamido | COOH | —CH$_2$SO$_3$K |
| 2-aminothiazol-4-yl-acetamido | CH$_3$ | —CH$_2$SO$_3$K |

In general, many of the compounds of the formula 1 are prepared directly in a two-step process in which an α,δ-alkanedicarboxylic acid mono ester, substituted β- to the free carboxy group, or an δ-protected amino alkylcarboxylic acid, substituted β- to the carboxy group, is converted to an O-substituted hydroxamate with an O-substituted hydroxylamine. The O-substituted hydroxamate is cyclized to the substituted β-lactam via displacement of the β-substituent by the nitrogen of the neighboring hydroxamate. The starting alkanecarboxylic acid, in addition to the β-substituent, can be substituted on one or more other carbon atoms. The β-lactam products obtained via the process are either represented by the formula 1 or are converted to β-lactams of the formula 1.

According to the process of this invention a β-substituted alkylcarboxylic acid represented by the formula 2

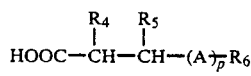  (2)

wherein
R$_4$ is hydrogen, hydroxy, protected amino, azido, C$_1$–C$_4$ alkyl, or C$_1$–C$_4$ alkoxy;
R$_5$ is hydroxy, acetoxy, halo-substituted acetoxy, C$_1$–C$_4$ alkylsulfonyloxy, arylsulfonyloxy, chloro, bromo, or iodo;
p is 0, 1 or 2;
A is a divalent radical represented by the formula

wherein
A' is hydrogen, C$_1$–C$_4$ alkyl, or C$_1$–C$_4$ alkoxyoarbonyl; and
R$_6$ is C$_1$–C$_4$ alkyl, protected amino, protected carboxy, or C$_1$–C$_4$ alkoxycarbonyl;
is reacted with an O-substituted hydroxylamine represented by the formula

wherein R$_3$ is other than hydrogen or the group

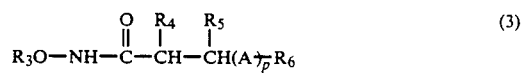

as defined hereinabove, to form the O-substituted hydroxamate represented by the formula 3.

  (3)

The O-substituted hydroxamate is then cyclized to the azetidin-2-one represented by the formula 4.

$$\begin{array}{c} R_4 \\ \diagup \\ O= \\ \end{array} \begin{array}{c} (A)_p R_6 \\ \diagdown \\ N \\ \diagdown \\ OR_3 \end{array} \quad (4)$$

The preparation of the O-substituted hydroxamate (3) is carried out in an aqueous medium maintained at a pH of between about 4.0 and about 5.0 in the presence of an excess of a carbodiimide. In carrying out the reaction the O-substituted hydroxylamine is generated in situ from the O-substituted hydroxylamine hydrochloride salt form.

Preferably, the pH of the reaction mixture is maintained at about pH 4.5. The carbodiimide is used in excess preferably in a two to three molar excess of the hydroxylamine. The reaction proceeds rapidly at temperatures between about 20° C. and about 40° C.

Carbodiimides which can be used in the preparation of the hydroxamates can be water soluble or nonwater soluble diimides. Examples of water soluble diimides are N-cyclohexyl-N'-(2-morpholinoethyl)carbodiimide p-toluenesulfonate, N-ethyl-N'-(3-dimethylaminopropyl)carbodiimide, and N-cyclohexyl-N'-(3dimethylaminopropyl)carbodiimide. The non-water soluble carbodiimides are used in a mixed aqueous organic solvent media e.g. tetrahydrofuran-H2O, 1:1, v:v. at an apparent pH of about 4 to about 5. Examples of such diimides include N,N-dicyclohexylcarbodiimide, N,N'-diethylcarbodiimide, N,N'-di-n-butylcarbodiimide, N,N'-diallylcarbodiimide, N,N'-diisopropylcarbodiimide, and N-cyclohexyl-N'-allylcarbodiimide. A preferred water soluble carbodiimide is N-ethyl-N'-(3-dimethylaminopropyl)carbodiimide.

The O-substituted hydroxamate (3) is then cyclized to the azetidin-2-one (4) as shown in the following scheme.

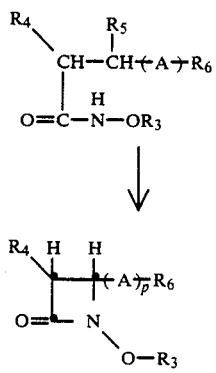

The cyclization conditions are dependent on the nature of the displaceable substituent group $R_5$. When $R_5$ is hydroxy the cyclization is carried out by dehydrative coupling with an azodicarboxylic acid diester and triphenylphosphine. When $R_5$ is chloro, bromo or an esterified hydroxy group (haloacetyl or an alkyl or arylsulfonyloxy group) the cyclization is carried out in the presence of a base.

The preferred method of cyclization is dehydrative coupling of $\beta$-hydroxy-substituted hydroxamate (formula 3, $R_5$=OH). The cyclization is carried out under anhydrous conditions in an inert solvent at a temperature between about 15° and about 35° C. The reagents, triphenylphosphine, and the azodicarboxylate are used in amounts equimolar with the hydroxamate, although a slight excess of either or both reagents can be used. Inert solvents which can be used include tetrahydrofuran, dioxane, and the ethers of ethylene glycol such as the dimethyl ether.

The preferred azodicarboxylate is diethyl azodicarboxylate (DEAD) and the preferred solvent is tetrahydrofuran.

When in the formula 3 $R_5$ is other than hydroxy, the cyclization is carried out in an inert solvent in the presence of a base. Inert solvents which can be used are the halogenated hydrocarbons such as methylene chloride, ethylene chloride, or trichloroethane, and amide solvents such as dimethylformamide and dimethylacetamide, or nitriles such as acetonitrile. Combinations of solvents also can be used e.g., DMF in methylene chloride is a desirable combination.

Bases which can be used in the cyclization of the hydroxamate when $R_5$ is other than hydroxy include the inorganic bases such as the alkali metal carbonates and bicarbonates, the alkali metal hydroxides and alkoxides, alkali metal hydrides, and the tertiary amines. Examples of such bases are sodium carbonate, sodium bicarbonate, potassium carbonate, potassium bicarbonate, sodium hydroxide, potassium hydroxide, sodium methylate, and sodium ethylate. When an alkali metal alkoxide is used as the base only one equivalent is employed. One equivalent is sufficient to remove the hydroxamate proton and generate the $-N^-OR_3$ anion. An excess of the alkoxide could disrupt the $\beta$-lactam ring following cyclization. Tertiary amines such as the trialkylamines e.g. triethylamine can also be used. When $R_5$ is halo, e.g. bromo, sodium hydride is a preferred base. Although a number of bases can be employed with any $R_5$ group, in general, the good leaving groups require only a weak base. For example, when $R_5$ is mesylate derivative, the cyclization can be carried out with an alkali metal bicarbonate in an aqueous medium. Preferably when $R_5$ is a $C_1-C_4$ sulfonyloxy group such as the methanesulfonyloxy group and $R_1$ is an acylamino group such as phenylacetylamino, the cyclization is carried out with potassium t-butoxide in dimethyl formamide at a temperature between about 0° C. and about −35° C.

Examples of $\beta$-substituted alkanedicarboxylic acid mono esters represented by the formula 2 are malic acid monobenzyl ester, malic acid monomethyl ester, malic acid monoethyl ester, malic acid monoisopropyl ester, bromosuccinic acid mono(4-nitrobenzyl)ester, ethylmalic acid monomethyl ester, ($R_4$=ethyl, $R_5$=OH, p=0, $R_6$=methoxycarbonyl), azidomalic acid monomethyl ester ($R_4$=N3, $R_5$=OH, p=0, $R_6$=methoxycarbonyl, erythro-$\beta$-hydroxyaspartic acid monomethyl ester ($R_4$=amino, $R_5$=OH, p=0, $R_6$=methoxycarbonyl), threo-$\beta$-hydroxyaspartic acid monoethyl ester, $\beta$-hydroxyglutamic acid monobenzyl ester ($R_4$=amino, $R_5$=OH, p=1, A'=H, $R_6$=benzyloxycarbonyl), N-(t-BOC)-$\beta$-hydroxyaspartic acid monomethyl ester, $\beta$-hydroxyglutaric acid monomethyl ester, tartaric acid monomethyl ester, $\beta$-hydroxy-$\delta$-methyladipic acid mono-(4-nitrobenzyl) ester, $\alpha$-amino-$\beta$-bromoadipic acid monoethyl ester, $\alpha$-methyl-$\beta$-hydroxyadipic acid monobenzyl ester, $\alpha,\beta$-dihydroxyglutaric acid monoethyl ester, and $\beta$-hydroxy-$\delta$-ethoxycarbonyladipic acid monoethyl ester.

Examples of $\omega$-protected amino-$\beta$-substituted alkanecarboxylic acids which are used in the process are $\beta$-hydroxy-$\gamma$-(t-butyloxycarbonylamino)butyric acid, $\beta$-hydroxy-$\delta$-(benzyloxycarbonylamino)valeric acid, $\beta$-bromo-$\delta$-(t-butyloxycarbonylamino)valeric acid, $\beta$-hydroxy-$\delta$-methyl-$\delta$-(p-nitrobenzyloxycarbonylamino)valeric acid, $\alpha,\beta$-dihydroxy-$\delta$-(t-butyloxycarbonylamino)valeric acid, $\alpha$-methyl-$\beta$-hydroxy-$\gamma$-(benzyloxycarbonylamino)butyric acid, and like substituted $\omega$-protected aminocarboxylic acids.

A preferred embodiment of the above-described process for preparing compounds of the invention comprises the use of a mono ester of malic acid or a substituted malic acid. For example, a malic acid mono ester represented by the formula,

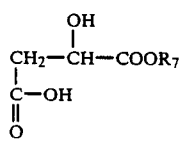

wherein $R_7$ is $C_1-C_4$ alkyl or a carboxy-protecting group, is converted to the hydroxamate represented by the formula

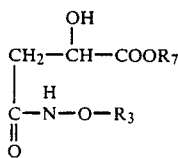

wherein R₃ is other than hydrogen or

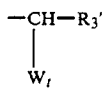

as defined hereinabove, and the hydroxamate is cyclized by dehydrative coupling with triphenylphosphine and diethyl diazodicarboxylate to provide the β-lactam compound represented by the formula

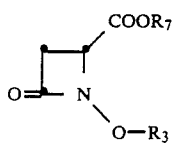

Preferred R₃ groups for use in the above embodiment are benzyl and pivaloyl.

Another preferred embodiment of the above-described process comprises the use of β-hydroxyaspartic acid mono ester represented by the following formula.

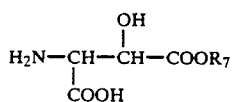

The amino acid is converted to the O-substituted hydroxamate as described above, and the hydroxamate is cyclized by the dehydrative coupling method to provide the 3-aminoazetidin-2-one represented by the formula

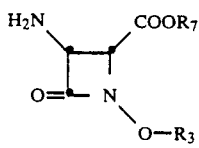

wherein R₇ and R₃ have the same meanings as defined hereinabove. For best results in this embodiment the amino group of the aspartic acid is protected prior to hydroxamate formation. For example, the amino group can be protected by the t-BOC group. Preferably, R₃ is benzyl, or pivaloyl, and R₇ is methyl or a carboxy-protecting group such as diphenylmethyl. The β-hydroxyaspartic acid can be in either the erythro or threo form.

In another preferred embodiment of the process a C₁-C₄ alkyl substituted malic acid mono ester is converted to the O-substituted hydroxamate and the latter is cyclized by dehydrative coupling to the 3-alkyl substituted β-lactam represented by the formula

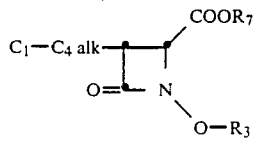

Preferably, R₃ is benzyl, 4-nitrobenzyl, 4-methoxybenzyl or pivaloyl.

The 3,4-disubstituted azetidin-2-ones represented by the formula 1 can be prepared in either the cis or trans form. For example, 1-methoxy-3-amino-4-methoxycarbonylazetidin-2-one can be prepared in either of the isomeric forms represented by the following formulas

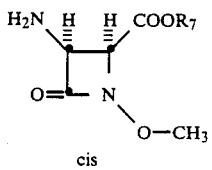

cis

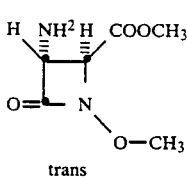

trans

As described hereinabove, a mono ester (formula 2, R₆ is C₁-C₄ alkoxycarbonyl or protected carboxy) can be employed in the preparation of the compounds of the invention. As shown in the formula 2 the ω-carboxylic acid group is the esterified carboxy group (R₆) while the carboxy group.. 8 to the displaceable substituent R₅ is in the free acid form for conversion to the hydroxamate. In a further aspect of this invention there is provided a process for preparing the requisite mono ester of the formula 2 wherein p is 0 or 1. According to this method an alkanedicarboxylic acid represented by the formula

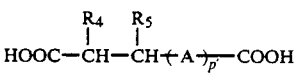

wherein R₄, R₅ and A have the same meanings as defined for formula 2 above and p' is 0 or 1, is converted to the 5- or 6-membered cyclic acid anhydride represented by the formula

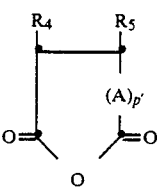

The anhydride of the above formula is then allowed to react with an alcohol, R₇OH, to provide the mono ester of the formula

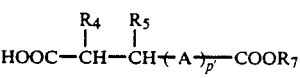

wherein p' and $R_7$ have the same meanings as defined above.

In the first step of the process, the dicarboxylic acid is converted to the cyclic anhydride by the reaction of the diacid with a dehydrating agent selected from a carbodiimide and trifluoroacetic anhydride.

The reaction is carried out under anhydrous conditions at a temperature of between about $-5°$ C. and about 45° C.

When carried out with a carbodiimide the anhydride formation is conducted in an inert solvent preferably at a temperature of about 20° C. to about 35° C. Carbodiimides which can be used are represented by the formula $$R_8-N=C=N-R_9$$

wherein $R_8$ and $R_9$ independently may be a $C_1$-$C_{12}$ aliphatic radical, a $C_3$-$C_7$ cycloaliphatic radical, phenyl, or $C_1$-$C_{12}$ alkyl substituted by phenyl. Such radicals may be for example, methyl, ethyl, n-propyl, allyl, isopropyl, n-butyl, sec-butyl, iso-butyl, tert-butyl, crotyl, amyl, hexyl, heptyl, octyl, isooctyl, nonyl, decyl, undecyl, dodecyl, cyclopropyl, cyclobutyl, cyclopentyl, cyclopentenyl, cyclohexyl, cyclohexenyl, cycloheptyl, phenyl, benzyl, phenethyl, and the like. The carbodiimides are readily prepared by a variety of methods known to the art.

Illustrative carbodiimides include N,N'-diethylcarbodiimide, N,N'-di-n-propylcarbodiimide, N,N'-diisopropylcarbodiimide, N,N'-di-n-butylcarbodiimide, N,N'-diallylcarbodiimide, N-propyl-N'-allylcarbodiimide, N,N'-dicyclohexylcarbodiimide, N-benzyl-N'-cyclohexylcarbodiimide, and the like. A preferred carbodiimide is dicyclohexylcarbodiimide.

The carbodiimide is preferably used in an amount corresponding to a slight molar excess, e.g. 1.1 moles of diimide for each mole of diacid.

When anhydride formation is carried out with trifluoroacetic anhydride (TFAA) the use of an aprotic solvent can be beneficial in large scale preparations. However, excess TFAA itself can also serve as the solvent. With TFAA the process is preferably carried out at a temperature between about 0° C. and about 15° C.

During the formation of the anhydride any free hydroxyl groups present in the diacid (for example when $R_5$ is hydroxy) are esterified with the reagent to trifluoroacetates.

Prior to the second step of the process, the cyclic anhydride is preferably separated from excess TFAA and trifluoroacetic acid by evaporation of the reaction mixture. When a diimide is used the anhydride is separated from the urea formed in the reaction with the diimide.

The cyclic anhydride is then mixed with the alcohol, $R_7OH$, to form the monoester represented by the above formula. The reaction can be conducted in an excess of a liquid alcohol or in an inert solvent with a solid alcohol. The alcohol reacts rapidly with the anhydride at or about room temperature to provide the desired mono ester in high yields.

Examples of alcohols, $R_7OH$, which can be used are the $C_1$-$C_4$ alkyl alcohols such as methyl alcohol, ethyl alcohol, n-propyl alcohol, isopoyl alcohol, n-butyl alcohol, tert-butyl alcohol, and the like; and alcohols which form carboxy-protecting groups such as for example, benzyl alcohol, p-nitrobenzyl alcohol, p-methoxybenzyl alcohol, diphenylmethyl alcohol, 2,2,2-trichloroethyl alcohol, and the like.

Inert solvents which can be used in the formation of the anhydride are for example, ethers such as tetrahydrofuran and dioxane; the halogenated hydrocarbons such as methylene chloride, dichloroethane, and the like.

Examples of alkanedicarboxylic acids which can be used in the process include the following: malic acid, bromosuccinic acid, β-hydroxyglutaric acid, β-bromoglutaric acid, α-methylmalic acid, α-ethylmalic acid, α-n-propylmalic acid, O-trifluoroacetylmalic acid, O-chloroacetylmalic acid, O-methanesulfonylmalic acid, O-tosylmalic acid, α-methoxymalic acid, α-azidomalic acid, α-azido-β-hydroxyglutaric acid, and α-ethyl-β-hydroxyglutaric acid.

In an example of the process wherein the cyclic anhydride is formed with a diimide, D-malic acid is dissolved in tetrahydrofuran and 1.1 molar equivalents of dicyclohexylcarbodiimide are added to the solution. The reaction mixture is stirred for about an hour and is then filtered to remove the precipitate of dicyclohexylurea. An excess (ca. 1.5 to 2.0 equiv.) of benzyl alcohol is added to the filtrate containing the malic acid cyclic anhydride and the solution is stirred for about 6 to about 12 hours. The reaction mixture is evaporated and the impure monobenzyl malate is dissolved in a water immiscible solvent such as ethyl acetate. The product is extracted with a base such as aqueous sodium bicarbonate, and after acidification of the extract the ester is extracted with ethyl acetate or other suitable solvent. The extract is dried and evaporated to yield the monobenzyl ester of malic acid represented by the formula $$\text{HOOC}-\text{CH}_2-\overset{\overset{\text{OH}}{|}}{\text{CH}}-\text{COOCH}_2\text{-phenyl}$$

In an example of the above process wherein trifluoroacetic anhydride (TFAA) is employed, L-malic acid is dissolved in excess TFAA at a temperature of about 0° C. to 5° C. and the solution is stirred in the cold for about 2 to 5 hours. The TFAA is removed by evaporation under reduced pressure in the cold to provide the anhydride as the trifluoroacetate. The anhydride is then dissolved in dry methyl alcohol and the solution is stirred at about room temperature for 3–5 hours to provide the desired monomethyl ester as illustrated in the following scheme.

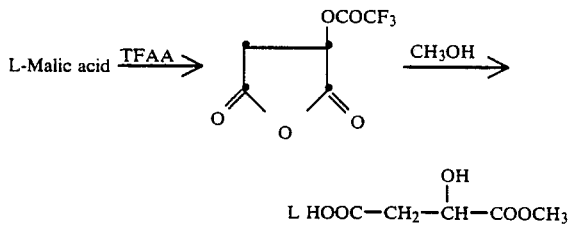

$$\text{L HOOC}-\text{CH}_2-\overset{\overset{\text{OH}}{|}}{\text{CH}}-\text{COOCH}_3$$

The monocyclic β-lactam compounds, represented by the formula 4, which are obtained in the above-described cyclization process are themselves compounds of the invention (formula 1) or they are converted to formula 1 compounds by known procedures. For example, when $R_4$ of the formula 4 is hydroxy, acylation of the hydroxy group with a $C_1$-$C_5$ alkanoyl halide, a benzoic acid halide or active ester provides the compounds of formula 1 wherein $R_1$ is $C_1$-$C_5$ alkanoyloxy, benzoyloxy, or substituted benzoyloxy.

Etherification of the compound of formula 4 wherein $R_4$ is hydroxy provides the formula 1 compounds wherein $R_1=C_1-C_4$ alkoxy. N-Acylation of the 3-amino group of the compounds of formula 4 wherein the protected amino, $R_4$, is deprotected provides the substituted amino compounds of the formula 1 wherein $R_1'$ is an acyl group and $R_1''$ is hydrogen. The N-acylation is carried out by coupling the appropriate carboxylic acid with the aminoazetidine-2-one. The acylation is carried out by following acylation procedures commonly employed in the N-acylation of 6-aminopenicillins and 7-aminocephalosporins. Preferably, the carboxy group of the carboxylic acid is first converted to an active derivative such as an acid halide, an acid azide, or an active ester. Acid halides, for example, the acid chloride or acid bromide, are coupled with the 3-aminoazetidinone in the presence of an acid-binding agent such as an inorganic base e.g. sodium carbonate, or a tertiary amine e.g. triethylamine. Other active derivatives of the carboxylic acid which can be used in the acylation include, for example, those formed with methyl chloroformate, ethyl chloroformate, or isobutyl chloroformate; and the active esters formed with N-hydroxy heterocyclics, for example, N-hydroxysuccinimide and N-hydroxybenzotriazole. During the N-acylation any other free amino or free hydroxy groups present in the 3-aminoazetidin-2-one are desirably protected to avoid any concomitant O-acylation or N-acylation at an undesired site in the molecule. In an example of an N-acylation of a 3-aminoametidin-2-one, 1-benzyloxy-3-amino-4-methoxycarbonylazetidin-2-one is reacted in acetonitrile with phenoxyacetyl chloride in the presence of triethylamine to provide 1-benzyloxy-3-phenoxyacetylamino-3-methoxycarbonylazetidin-2-one. In a further acylation example, 1-pivaloyloxy-3-amino-4-(methylsulfonyloxynethyl)azetidin-2-one is dissolved in acetonitrile and tetrahydrofuran and reacted with the enamine-protected active derivative of D-phenylglycine formed with ethyl acetoacetate and methyl chloroformate as illustrated in the following reaction scheme.

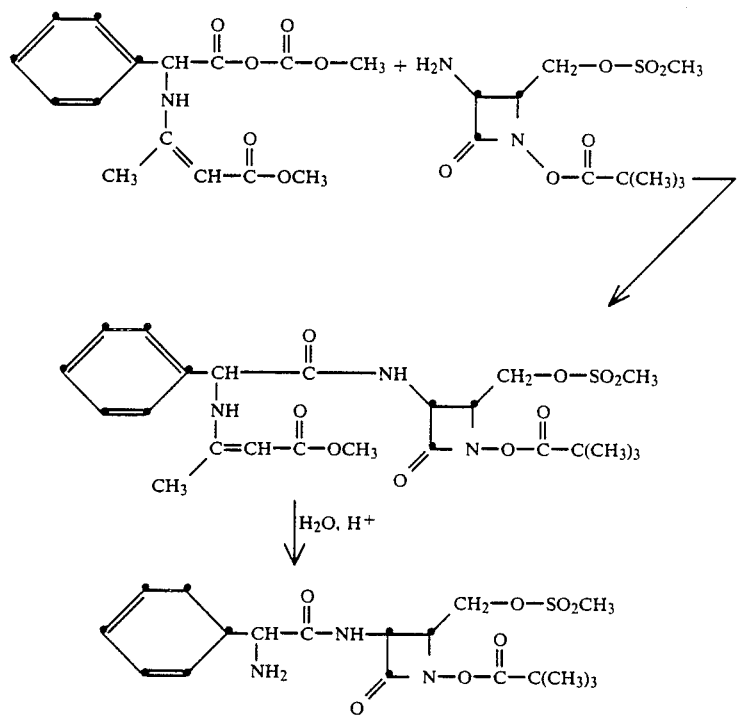

In yet a further example of the preparation of compounds of the formula 1 by N-acylation of a 3-aminoazetidinone, 1-pivaloyloxy syn-3-[2-(2-aminothiazol-4-yl)-2-methoxyiminoacetamido]-4-[2-(4-nitrobenzyloxycarbonyl)ethyl]-azetidin-2-one is prepared by the acylation of 1-pivaloyloxy 3-amino-4-[2-(4-nitrobenzyloxycarbonyl)ethyl]azetidinone with the hydroxybenzotriazole (HBT) ester of syn-2-(2-aminothiazol-4-yl)-2-methoxyiminoacetic acid as shown below.

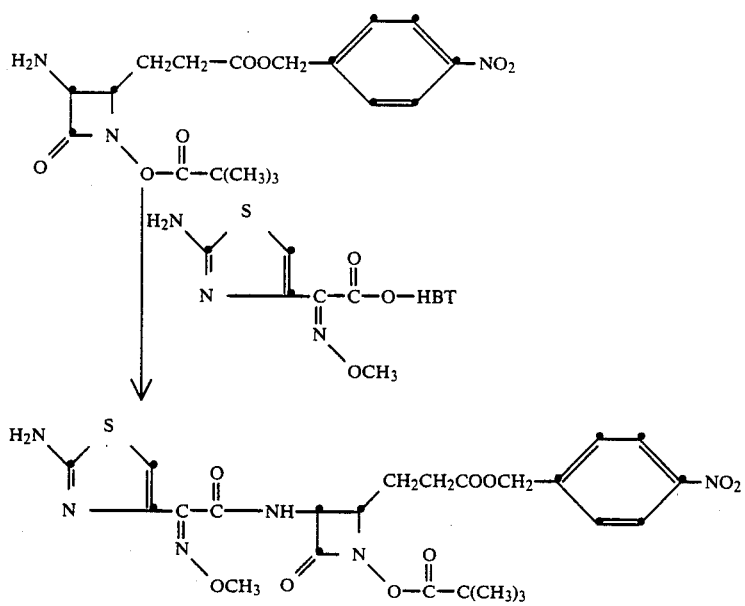

Compounds represented by the formula 1 wherein $R_1$ is an acylamino group are also obtained with a compound of the formula 4 wherein $R_4$ is an azido group. Reduction of the azido group provides the 3-aminozetidin-2-one which on N-acylation with the appropriate carboxylic acid provides the compound of formula 1 wherein $R_1$ is an acylamino group.

The substituent groups in the 4-position of the azetidin-2-one ring (formula 1, $R_2$) are the substituents $-(A)_{\overline{p}}R_6$ of formula 4 (products of the process described above) or are obtained therefrom by chemical conversion. For example, saponification of a $C_1$-$C_4$ alkoxycarbonyl group ($R_6$) affords the corresponding carboxy substituent ($R_2$ formula 1) which can be converted to a salt form. The esterified carboxy also can be reduced, e.g. with borohydride, to provide the corresponding alcohol, for example, a 3-ethoxycarbonylazetidin-2-one is reduced to a 3-hydroxymethylazetidin-2-one.

The hydroxyalkyl substituent $R_2$ (formula 1) can be halogenated, esterified or etherified to provide the corresponding haloalkyl, ester, or ether substituent represented by $R_2$.

The compounds represented by the formula 1 wherein $R_3$ is

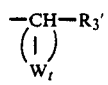

are prepared with the N-hydroxyazetidinones (formula 1, $R_3$=hydrogen). The sulfate esters, $R_3$ is $-SO_3M$, are obtained when the N-hydroxy compound is allowed to react at a temperature between about 0° C. and about 35° C. with the complex formed with sulfur trioxide and pytidine or dimethyl formamide. The reaction is preferably carried out in an excess of the pyridine or DMF used to form the complex. The reaction is illustrated as follows:

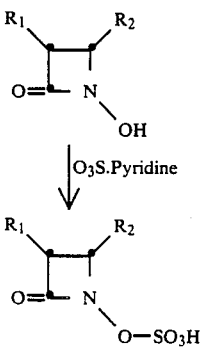

The sulfate ester preparation can be carried out in the presence of ammonia or a trialkylamine and the product isolated as the corresponding ammonium or trialkylammonium salt thereof. Alternatively, the acid product can be converted to the more stable salt form on a cationic exchange resin. The sodium or potassium salts can be obtained in this manner. During the preparation any free amino and carboxy groups present in the starting material are desirably protected.

A preferred method for preparing the sulfate esters employs the $SO_3$.pyridine complex. In carrying out the reaction the N-hydroxy azetidinone is dissolved or suspended in excess pyridine and a slight excess of sulfur trioxide is added. Alternatively, the preformed complex in pyridine can be added to the N-hydroxy compound in pyridine. The latter procedure can also be carried out by reverse addition.

The phosphate esters (formula 1, $R_3'$ is $-P(C=O)(OM')_2$ and $t=0$, are prepared by reacting the N-hydroxyazetidinone in an inert organic solvent with diphenyl chlorophosphate in the presence of one equivalent of an organic base to provide the diphenyl phosphate ester. The preparation is shown in the following reaction scheme.

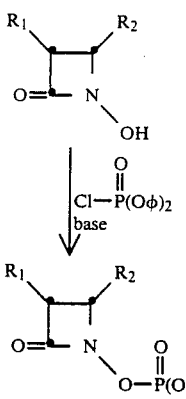

The diphenyl phosphate derivative is then subjected to hydrogenolysis over platinum oxide and hydrogen in an inert solvent to provide the desired mono ester as shown below.

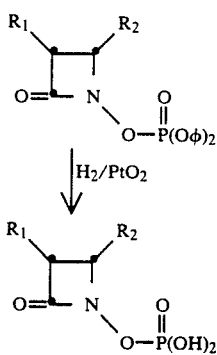

The preparation of the azetidinone diphenyl phosphate ester is carried out in the presence of an organic base such as a trialkylamine or pyridine. The base serves as a hydrogen chloride acceptor. Pyridine is a preferred base in the reaction.

Inert organic solvents which can be used are those solvents which are unreactive toward the chlorophosphate and in which the azetidinone and the chlorophosphate are at least partially soluble. Organo nitriles such as acetonitrile are suitable solvents.

The hydrogenolysis of the diphenyl phosphate product can be carried out at ambient temperature or at slightly elevated temperatures up to about 40° C. to 45° C. in a suitable solvent-such as ethyl alcohol. The acidic product wherein M' is hydrogen can be converted to an alkali metal or alkaline earth metal salt, or to the diammonium salt of a di(-substituted)ammonium salt.

The 1-hydroxyazetidin-2-ones represented by the formula 1 wherein $R_3$ is hydrogen are prepared with the compounds of formula 1 wherein $R_3$ is other than hydrogen. For example, the 1-benzyloxyazetidin-ones undergo hydrogenolysis to the 1-hydroxyazetidin-2-ones over 5% Pd/C under hydrogen. When $R_3$ is pivaloyl the 1-pivaloyloxyazetidinones undergo hydrolysis to the 1-hydroxyazetidinones.

When $R_3'$ is a 1H-tetrazole ring and t=0, the compounds represented are prepared by reacting a 5-halo-1H-tetrazole with the 1-hydroxy β-lactam in the presence of a base. When t=1-4, the compounds are prepared with a 5-haloalkyl-1H-tetrazole, e.g. 5-chloromethyl-1H-tetrazole, by O-alkylation of the 1-hydroxyazetidinone in the presence of a base. During the O-alkylation the acidic hydrogen in the 1-position of the tetrazole ring is desirably protected, e.g. with benzyl, substituted benzyl, or other suitable blocking group.

When $R_3'$ is $-SO_3M$, $-O-SO_3M$, $PO_3M'$ or

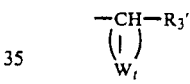

the corresponding haloalkyl derivative or ω-substituted haloalkyl derivative is employed in the O-alkylation. The more reactive bromoalkyl derivatives are preferred, although the chloroalkyl derivatives can be used also.

The 1-hydroxyazetidin-2-ones are also prepared by the process described in copending application Ser. No. 479,375, filed Mar. 28, 1983. According to this process, a β-hydroxy alkylcarboxylic acid (formula 2) is converted to the hydroxamic acid, the latter is acetylated with acetic anhydride and the O-acetyl hydroxamate derivative is cyclized to the 1-acetoxy-2azetidinone with triphenylphosphine and DEAD. Mild aqueous hydrolysis of the cyclized product with sodium carbonate provides the 1-hydroxy-2-azetidinone.

The compounds represented by, the formula 1 wherein $R_3$ is a group of the formula

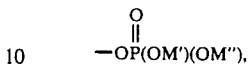

and t is 1–4, are prepared by the, O-alkylation of a 1-hydroxyazetidinone-2 with a halo derivative of the formula

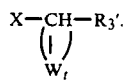

The O-alkylation is carried out with a base such as an alkali metal carbonate, an alkali metal hydroxide, sodium hydride, an alkali metal alkoxide or other suitable base. For example when $R_3'$ is a protected carboxy group, a carboxy-protected ω-haloacetic acid, or such an acid substituted by W; e.g. a carboxy-protected bromoacetic acid, bromopropionic acid, and the like is reacted with the 1-hydroxyazetidinone with potassium carbonate to form the 1-carboxyalkoxy O-alkylation product having a protected carboxy group.

The 1-hydroxyazetidinones represented by the formula 1 wherein $R_3$ is hydrogen are reduced to the 1-unsubstituted azetidin-2-ones with titanium trichloride in an aqueous medium at pH 4 to 10 by the procedure described by Miller et al., *J. Amer. Chem. Soc.*, 102, 7026 (1980).

The conversion of a compound of the invention to a 1-unsubstituted azetidinone in illustrated in the following reaction scheme wherein $R_3$ is benzyl.

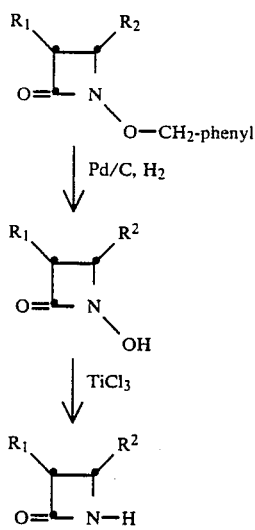

The 1-unsubstituted azetidinones can also be prepared with the compounds represented by the formula 1 wherein $R_3$ is $C_1-C_4$ alkyl, by treatment of the latter compounds with sodium in liquid ammonia.

The 1-unsubstituted azetidinones obtained by the removal of the $OR_3$ group of the compounds represented by the formula 1 are versatile intermediates useful for the preparation of β-lactam antibiotics and compounds having β-lactamase activity. For example, they are useful in the preparation of monocylic β-lactam antibiotics substituted on the nitrogen of the β-lactam ring by $-SO_3^-M^+$ as described in Netherlands published application No. 8100571 published Sept. 1, 1981. The compounds of the invention are also useful in the preparation of the 1-substituted-3-azido and 3-amino-4-(2-formylethyl)azetidinones disclosed in British Patent Specification No. 1,592,333. The compounds of the invention are also useful in the preparation of thienamycin intermediates such as the 3-(1-acyloxyethyl)-4-carboxymethylazetidin-2-ones disclosed in EPO application 32-400 (Derwent publ. abst. No. 55466).

The N-oxy compounds represented by the formula 1 also can be converted to 1-unsubstituted azetidinones useful in the preparation of the products and intermediates described in U.S. Pat. Nos. 4,000,154, 4,072,674, 4,122,262, 4,162,250, 4,187,375, 4,200,572, 4,181,800, 4,093,807, 4,310,538, and numerous other patents.

Certain of the N-oxy β-lactam compounds of the invention are preferred. A preferred group of compounds are represented by the formula 1 wherein $R_1$ is amino. These 3-aminoazetidinones are represented by the formula

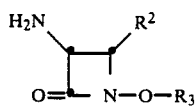

A further preferred group of intermediates are represented by the above formula wherein $R_3$ is hydrogen and the amino group is protected. The β-lactam compound of the above formula can be in either the cis or trans form by virtue of the configuration of the B-substituted diacid employed in the process described herein.

Another preferred group of compounds is represented by the formula 1 wherein $R_1'$ is an acyl group of the formula

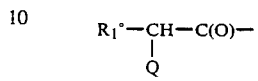

wherein Q is amino, hydroxy, formyloxy, or carboxy.

Compounds of the formula 1 having the acyl group represented by the above formula wherein Q is a substituted amino group represented by the formula

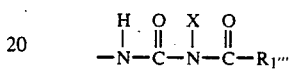

wherein $R_1'''$ is as defined above are prepared by the acylation of a compound wherein Q is amino with a chlorocarbonyl derivative of the formula

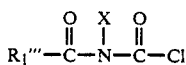

For example, N-chlorocarbonyl-N-methylbenzamide (formula 1, $R_1°=R_1'''=$phenyl, x=methyl) is allowed to react with 1-benzyloxy-3-phenylglycylamino-3-(2-benzyloxycarboxy)ethylazetidin-2-one to provide the compound

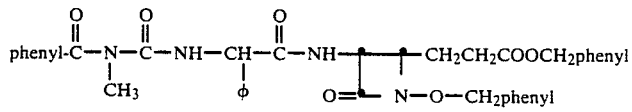

When $R_1'''$ is a group of the formula

the compounds represented are prepared in the same manner. For example, the carbonyl chloride of the formula

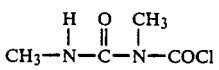

is allowed to react with phenylglycyl-substituted compound to provide a compound of the formula

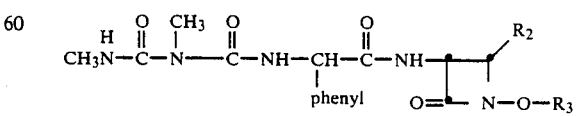

(formula 1, $R_1°=$phenyl, $R_1''''$ is methyl, x=H, y=-methyl).

Likewise, compounds wherein x and y together form a 5- or 6-membered ring are prepared with the corresponding N-carbonyl chlorides represented by the formula

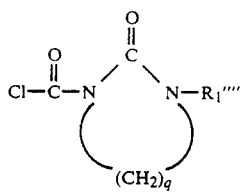

Other acylamino substituted β-lactams of the invention which are preferred are represented by the formula wherein R' is methyl or —C(CH$_3$)$_2$COOH and the oximino group is preferably syn, and wherein R$_2$, W, t, and R$_3$' the same meanings as hereinabove. In particular, R$_3$' is preferably a carboxy group COOR$_3$", W is hydrogen and t is 1 or 2. Compounds wherein R$_2$ is hydrogen, methyl, carboxy or protected carboxy are further preferred members of the group. Examples of these preferred compounds include 1-(carboxymethoxy)-3β-[2-(2-aminothiazol-4-yl)-2-methoxyiminoacetamido]-2-azetidinone, 1-(carboxymethoxy)-3β-[2-(2-aminothiazol-4-yl)2-methoxyiminoacetamido]-4α-methyl-2-azetidinone, 1-(2-carboxyethoxy)-3β-[2-(2-aminothiazol-4-yl)-2-methoxyiminoacetamido]-4α-methyl-2-azetidinone, 1-(carboxymethoxy)-3β-[2-(2-

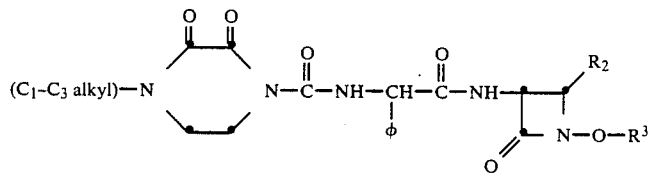

These compounds are prepared by the N-acylation of the formula 1 compound wherein Q is amino. The acylation is carried out with the N-chlorocarbonylpiperazine-2,3dione having a lower alkyl group in the 4-position. The acylation is carried out in the presence of an acid-binding agent such as pyridine or triethylamine. Preferably, the piperazine-2,3-dione is a 4-ethylpiperazine-2,3-dione.

The R$_3$ substituent in the foregoing preferred groups of 3-acylamino-2-azetidinones is preferably one wherein R$_3$' is —SO$_3$M, W is hydrogen, and t is 0 or 1 or R$_3$' is —COOR$_3$", W is hydrogen, and t is 1 or 2.

A further preferred group of 3-acylamino-β-lactam compounds of this invention are represented by the formula

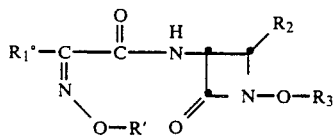

Especially preferred are compounds wherein R$_1$° represents the 2-aminothiazol-4-yl heterocyclic and R' is methyl or the carboxy-substituted alkyl group —C(CH$_3$)$_2$COOH.

Among these preferred compounds are those wherein R$_3$ is the group

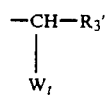

which are represented by the general formula

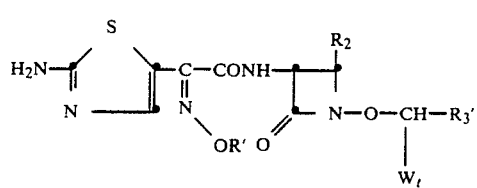

aminothiazol-4-yl)-2-methoxyiminoacetamido]-carboxy-2-azetidinone, 1-(carboxymethoxy)3β-[2-(2-iminothiazol-4-yl)-2-(2-carboxyprop)-2-oxyiminoacetamido]-4-ethoxycarbonyl-2-azetidinone, 1-(carboxymethoxy)-3β-[2-(2-aminothiazol-4-yl)-2-(2-carboxyprop)-2-oxyiminoacetamido]-3α-methyl-2azetidinone, and the sodium and potassium salt forms thereof.

The antibacterial spectrum for two of the preferred compounds mentioned above is shown in the following Table II.

TABLE II

| Antibacterial Activity Via Agar Dilution Method | | | |
|---|---|---|---|
| | | mic(μg/ml) compound | |
| Organism | Strain | A[1] | B[2] |
| Staphylococcus aureus | X1.1 | 64+ | 64+ |
| Staphylococcus aureus | V41 | 64+ | 64+ |
| Staphylococcus aureus | X400 | 64+ | 64+ |
| Staphylococcus aureus | S13E | 64+ | 64+ |
| Staphylococcus epidermidis | EP11 | 64+ | 64+ |
| Staphylococcus epidermidis | 222 | 64+ | 64+ |
| Streptococcus pyogenes | C203 | 16 | 16 |
| Streptococcus pneumoniae | Park | 32 | 32 |
| Streptococcus sp. Group D | X66 | 64+ | 64+ |
| Streptococcus sp. Group D | 2041 | 64+ | 64+ |
| Haemophilus influenzae | C.L. | 16 | 1 |
| Haemophilus influenzae | 76 | 16 | 1 |
| Escherichia coli | N10 | 8 | .25 |
| Escherichia coli | EC14 | 4 | .25 |
| Escherichia coli | TEM | 32 | .5 |
| Klebsiella pneumoniae | X26 | 8 | .25 |
| Klebsiella pneumoniae | KAE | 64+ | 32 |
| Klebsiella pneumoniae | X68 | 8 | .25 |
| Enterobacter aerogenes | C32 | 8 | .25 |
| Enterobacter aerogenes | EB17 | 8 | .25 |
| Enterobacter cloacae | EB5 | 16 | 1 |
| Enterobacter cloacae | 265A | 64+ | 64+ |
| Salmonella typhi | X514 | 4 | .125 |
| Salmonella typhi | 1335 | 8 | .25 |
| Pseudomonas aeruginosa | X528 | 64+ | 64+ |
| Pseudomonas aeruginosa | X239 | 64+ | 64+ |
| Pseudomonas aeruginosa | PS18 | 64+ | 64+ |
| Pseudomonas aeruginosa | PS72 | 64+ | 64+ |
| Serratia marcescens | X99 | 16 | .5 |
| Serratia marcescens | SE3 | 16 | 1 |
| Shigella sonnei | N9 | 8 | .25 |
| Proteus morganii | PR15 | 32 | 2 |
| Proteus inconstans | PR33 | 2 | .125 |
| Proteus rettgeri | C24 | 2 | .125 |
| Citrobacter freundii | CF17 | 16 | 2 |

TABLE II-continued

Antibacterial Activity Via Agar Dilution Method

| Organism | Strain | mic(μg/ml) compound A[1] | B[2] |
|---|---|---|---|
| *Acinetobacter calcoaceticus* | AC12 | 64+ | 64+ |

[1]compound A = 1-(carboxymethoxy)-3-[(z)-2-(2-aminothiazol-4-yl)-2-methoxyiminoacetamido]-2-azetidinone potassium salt.
[2]compound B = 1-(carboxymethoxy)-3β-[(z)-2-(2-aminothiazol-4-yl)-2-methoxyiminoacetamido]-4α-methylazetidin-2-one potassium salt.

The β-lactam compounds represented by the formula 1 wherein $R_3$ is a sulfate ester —$SO_3M$ or a phosphate ester —P(C=O)(OM')$_2$ inhibit the growth of microorganisms, including the gram-positive and gram-negative bacteria, pathogenic to man and animals. These monocyclic β-lactam compounds in the salt form can be used to control infections upon administration in a non-toxic therapeutically effective dose of from about 25 mg. to about 500 mg.

Examples of compounds wherein $R_3$ is —$SO_3M$ are represented by the following formula

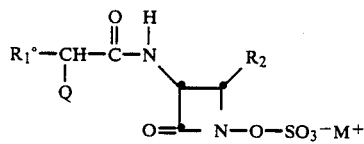

wherein $M^+$ is a sodium or potassium ion, $R_1°$ is phenyl, substituted phenyl, thienyl, furyl, or cyclohexadienyl; Q is hydrogen, hydroxy, amino, carboxy, or sulfo; and $R_2$ is hydrogen, $C_1$-$C_4$ alkyl, carboxy, or $C_1$-$C_4$ alkyl substituted by hydroxy, halo, or carboxy. For example, in the above formula $R_2$ can be methyl or ethyl and the acyl group of the 3-acylamino substituent can be phenylacetyl, mandeloyl, phenylglycyl, 3- or 4-hydroxyphenylglycyl, 2-(cyclohex-1,4-dienyl)-2-aminoacetyl, 2-(2-thienyl)-2-aminoacetyl, 2-carboxy-2-phenylacetyl, 2-sulfo-2-phenylacetyl, and the like.

Preferred sulfate esters of the above formula 1 are represented by the following formula

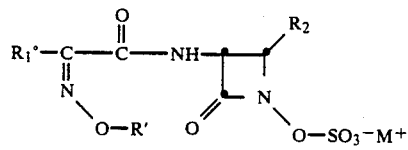

Wherein $M^+$ is sodium or potassium, $R_1°$ is 2-aminothiazol-4-yl, and $R_2$ is hydrogen or $C_1$-$C_4$ alkyl. Especially preferred are the compounds represented by the formulas

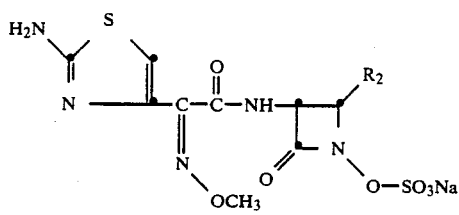

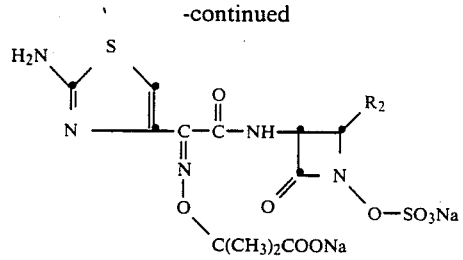

wherein $R_2$ is hydrogen, methyl, or ethyl.

Examples of phosphate esters (formula 1, $R_3$ is —P(C=O)(OM')$_2$ are represented by the following formulas

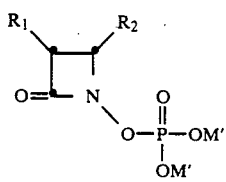

wherein M' is sodium or potassium, $R_2$ is hydrogen, $C_1$-$C_4$ alkyl, carboxy, or $C_1$-$C_4$ alkyl substituted by hydroxy, halo, or carboxy; and $R_1$ is an acylamino group

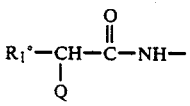

e.g. phenylacetylamino, D-phenylglycylamino, D-mandeloylamino, phenylmalonylamino;

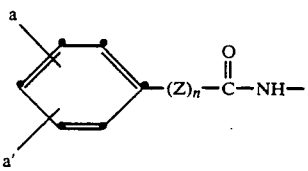

e.g. phenoxyacetylamino, 4-chlorophenoxyacetylamino, phenylmercaptoacetylamino;

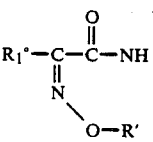

e.g. 2-(2-aminothiazol-4-yl)-2-methoxyiminoacetylamino; -(2-aminothiazol-4-yl)-2-(2-carboxyprop-2-yl)oxyiminoacetylamino, 2-(2-furyl)-2-methoxyiminoacetylamino, 2-(2-thienyl)-2-carboxymethoxyiminoacetylamino; and like azetidinones.

Especially preferred phosphate esters of the above formula are represented by the formulas

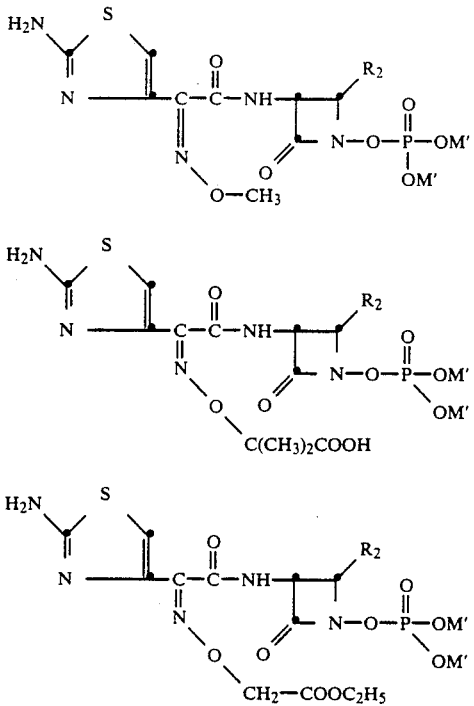

wherein M' is sodium or potassium and R₂ is hydrogen, methyl, or ethyl.

The following examples further illustrate the present invention. In the examples the following abbreviations are used:
MS=Mass Spectrometry
IR=Infrared Spectrum
UV=Ultraviolet Spectrum
DEAD=Diethyl Diazodicarboxylate
DCC=Dicyclohexylcarbodiimide
TFAA=Trifluoroacetic Anhydride
NMR=Nuclear Magnetic Resonance Spectrum Signals in the spectra: s=singlet, m=multiplet, d=doublet, q=quartet, t=triplet, br=broad signal.

Unless otherwise indicated NMR spectra were 60 MHz.

EXAMPLE 1

1-Benzyloxy-4-(benzyloxycarbonyl)azetidin-2-one

A. D-Malic acid monobenzyl ester

To a solution of D-malic acid (18.8 g., 140.2 mmole) in 150 ml. of freshly-distilled THF was added dicyclohexylcarbodiimide (DCC, 1.1 equiv.) and the mixture was stirred at room temperature for 45 minutes. The reaction mixture was filtered to remove the precipitate of dicyclohexylurea which formed. The precipitate was washed with two 50 ml. portions of THF and the washings were combined with the filtrate. To the combined filtrate and washings were added two equivalents of benzyl alcohol and the solution was stirred overnight at room temperature. The reaction mixture was evaporated to remove the solvent and the residual oil containing the monoester was dissolved in 100 ml. of ethyl acetate. The solution was extracted with three 50 ml. portions of a 10% solution of sodium carbonate in water and the extracts were combined, acidified to pH 2 and extracted with three 50 ml. portions of ethyl acetate. The extracts were combined, washed with 25 ml. of brine, dried over magnesium sulfate, filtered, and then evaporated to dryness to yield D-malic acid monobenzyl ester as an oil in 64% yield.

¹HNMR(CDCl₃): δ 2.85 (d, 2H, J=5.5), 4.55 (t, 1H, J=5.5), 5.2 (s, 2H), 7.35 (s, 5H), 7.5 (br. s, 2H, CO2H+OH).

IR (neat): 3100–3500 cm⁻¹ broad, 1735 cm⁻¹.

B. O-Benzyl D-malic acid hydroxamate monobenzyl ester

The monobenzyl ester of D-malic acid prepared as described above (2.14 g., 10 mmole) was dissolved in 35 ml. of water at pH 4.5 along with 11 mmole of O-benzylhydroxylamine hydrochloride. To the solution was added an aqueous solution containing 20 mmole of N-ethyl-N'-(3-dimethylaminopropyl)carbodiimide in water. An oil separated immediately from the mixture. After 30 minutes the reaction mixture was extracted with three 50 ml. portions of ethyl acetate and the extracts were combined and washed successively with two 20 ml. portions of 1M citric acid, 20 ml. of water, twice with 20 ml. portions of 5% sodium bicarbonate, and with 20 ml. of brine. The washed extract was dried over magnesium sulfate, filtered and then evaporated to yield 2.7 g. (84.5%) of O-benzyl D-malic acid hydroxamate monobenzyl ester as an oil. The product solidified on standing and melted at about 102° to about 104° C. after recrystallization from ether-hexane.

$[\alpha]_D^{20}$ = +27.2 (C=2.5, methanol)

IR (chloroform), 3200–3600 cm⁻¹ (br. OH, NH), 1745 cm⁻¹ (ester), 1690 cm⁻¹ (hydroxamate).

NMR (CDCl₃) δ 2.6 (br. d, 2H), 4.48 (t, 1H), 4.8 (s, 2H), 5.15 (s, 2H), 7.32 (s, 1H).

C. 1-Benzyloxy-4-(benzyloxycarbonyl)azetidin-2-one

The O-benzyl D-malic acid hydroxamate monoester (2.64 g., 8.02 mmole) prepared as described above was dissolved in 50 ml. of dry THF (freshly distilled) and triphenylphosphine (2.1 g., 8.02 mmole) was added to the solution followed by diethyl azodicarboxylate (DEAD, 1.26 ml.). The reaction mixture was stirred at room temperature under a drying tube for 11 hours and thereafter concentrated by evaporation to a volume of about 10 ml. The concentrate was chromatographed on a medium pressure HPLC apparatus (Michel-Miller column) with one liter of ethyl acetate:hexane, 20:80, v:v, and then the same solvents in a 50:50, v:v mixture. The product was obtained as an oil (2.40 g., 96% yield) following evaporation of the product containing fractions.

$[\alpha]_D^{20}$ = −12.6° (C=3.6, methanol).

IR (neat) 1745 cm⁻¹, 1780 cm⁻¹.

NMR (CDCl₃)δ 2.8 (m, 2H), 4.1 (m, 1H), 4.95 (s, 2H), 5.2 (s, 2H), 7.32 (s, 5H), 7.5 (s, 5H).

EXAMPLE 2

1-Benzyloxy-4-(methoxycarbonyl)azetidin-2-one

A. D-Malic acid monomethyl ester

By following the procedures described by Example 1A, D-malic acid was converted to the anhydride with DCC and the anhydride allowed to react with methyl alcohol to provide in 64.5% yield of the monomethyl ester melting at about 79° to about 80° C.

$[\alpha]_D^{20}$ = −5°±1 (C=9.5, methanol).

NMR (CDCl₃): δ 2.9 (d, 2H), 3.8 (s, 2H), 4.5 (t, 1H), 6.5–6.9 (br. OH, CO2H).

B. O-Benzyl D-malic acid hydroxamate monomethyl ester.

The monomethyl ester prepared as described above was reacted with O-benzylhydroxylamine hydrochloride and N-ethyl-N'-(3-dimethylaminopropyl)carbodiimide by following the procedures and reaction conditions of Example 1B. The O-benzyl D-malic acid hydroxamate monoester melting at about 65° to about 67° C. was obtained in 70% yield.

Elemental analysis (%) for $C_{12}H_{13}NO_4$: Calc.: C, 56.92; H, 5.93; N, 5.53 Found: C, 57.22; H, 5.67; N, 5.43.

NMR (CDCl$_3$): δ 2.6 (br., m, 2H), 3.75 (s, 3H), 4.5 (t, 1H), 4.87 (s, 2H), 7.37 (s, 5H).

C. 1-Benzyloxy-4-(methoxycarbonyl)azetidin-2-one

The O-benzyl malic acid hydroxamate monomethyl ester prepared as described above was cyclized to the azetidin-2-one by using the procedures, reagents and conditions described by Example 1C. The product was obtained as an oil in 78% yield.

NMR (CDCl$_3$): δ 2.8 (dd, 2H), 3.8 (s, 3H), 4.2 (dd, 1H), 5.1 (s, 2H), 7.4 (s, 5H).

EXAMPLE 3

L-1-Benzyloxy-4-(methoxycarbonyl)azetidin-2-one

A. L-Malic acid monomethyl ester

L-malic acid (10 g., 74.6 mmole) was placed in a 100 ml. round-bottom flask and cooled in an ice bath. Trifluoroacetic anhydride, TFAA, (25 ml.) was added to the flask and the suspension was stirred in the cold. Within 15 minutes a homogeneous solution was obtained. After stirring for 2 hours at a temperature of about 0° C., the TFAA and trifluoroacetic acid were removed by vacuum distillation at 0° C. The solid residue of L-malic anhydride trifluoroacetate represented by the formula

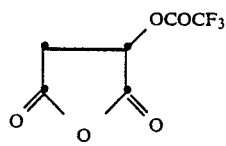

was dissolved in 50 ml. of anhydrous methyl alcohol and the solution stirred at room temperature for 3.5 hours. The solvent was removed by evaporation to provide in 100% yield L-malic acid monomethyl ester melting at about 75° to about 79° C. After recrystallization from ethyl acetate-hexane the product melted at about 79° to about 80° C. $[\alpha]_D^{20} = 5.8 \pm 1°$ (C=9.5, methanol).

The NMR spectrum was identical to that of the D-malic acid monomethyl ester (Example 2A).

B. O-Benzyl L-malic acid hydroxamate monomethyl ester

L-Malic acid monomethyl ester prepared as described in A is converted to the O-benzyl hydroxamate monoester derivative as in Example 2B.

C. L-1-Benzyloxy-4-(methoxycarbonyl)azetidin-2-one is prepared with the O-benzylhydroxamate methyl ester by using the reagents, procedures and conditions as described in Example 2C.

EXAMPLE 4

L-1-Benzyloxy-4-(ethoxycarbonyl)azetidin-2one

A. L-Malic acid monoethyl ester

By using the reagents, procedures and conditions described by Example 3A L-malic acid was converted to L-malic anhydride trifluoroacetate and the latter was allowed to react with ethyl alcohol to provide in 98.7% yield L-malic acid monoethyl ester melting at about 48° to about 49.5° C.

NMR (CDCl$_3$) δ1.3 (t, 3H), 2.9 (d, 2H), 4.3 (q, 2H), 4.57 (t, 1H), 7.5 (br. OH, CO$_2$H).

B. O-Benzyl L-malic acid hydroxamate monoethyl ester

By the use of the reagents, procedures and conditions described by Example 1B, L-malic acid monoethyl ester was reacted with O-benzyl hydroxylamine hydrochloride to provide a 60% yield O-benzyl L-malic acid hydroxamate monoethyl ester as an oil.

IR (neat) 3200–3600 cm$^{-1}$ (OH, NH), 1745 cm$^{-1}$ (ester), 1690 cm$^{-1}$ (hydroxamate).

NMR (CDCl$_3$)δ 1.25 (t, 3H), 2.68 (d, 2H), 4.23 (q, 2H), 4.42 (t, 1H), 4.85 (s, 2H), 7.32 (s, 5H).

C. 1-Benzyloxy-4-(ethoxycarbonyl)azetidin-2-one

The L-malic acid O-benzylhydroxamate was cyclized by using the procedures, reagents, and conditions described by Example 1C to provide in 88.5% yield 1-benzyloxy-4-(ethoxycarbonyl)azetidin-2-one as an oil.

IR (neat) 1740 cm$^{-1}$, 1785 cm$^{-1}$

NMR (CDCl$_3$)δ 1.25 (t, 3H), 2.8 (dd, 2H), 4.15 (m, C$_3$—H, C$_4$—H; and —OCH$_2$CH$_3$), 5.03 (s, 2H), 7.4 (s, 5H).

EXAMPLE 5

L-1-Benzyloxy-4-(isopropoxycarbonyl)azetidin-2-one

A. L-Malic acid monoisopropyl ester

By the use of the procedures and conditions described by Example 3A, L-malic acid was converted to L-malic anhydride trifluoroacetate with trifluoroacetic anhydride, and the anhydride allowed to react with isopropyl alcohol to provide in 97.7% yield L-malic acid monoisopropyl ester as an oil.

NMR (CDCl$_3$)δ 1.25 (d, 6H), 2.9 (d, 2H), 4.58 (t, 1H), 5.14 (m, 1H), 8.4 (s, br. OH and CO$_2$H).

B. O-Benzyl L-malic acid hydroxamate monoisopropyl ester

L-Malic acid monoisopropyl ester was converted to the O-benzyl hydroxamate as described in the preceding examples (Part B). The hydroxamate melting at about 75° to about 78° C. was obtained in 84% yield.

NMR (CDCl$_3$):δ 6 1.2 (d, 6H), 2.6 (br, 2H), 4.1 (m, 1H), 4.45 (t, 1H), 4.9 (s, 2H), 7.36 (s, 5H).

C. L-1-Benzyloxy-4-(isopropoxycarbonyl)-azetidin-2-one

O-Benzyl L-malic acid hydroxamate monoisopropyl ester is cyclized to the azetidin-2-one by using the reagents, reaction conditions, and procedures described by the preceding examples (Part C).

EXAMPLE 6

D,L-1-Methoxy-4-(4-nitrobenzyloxycarbonyl)-azetidin-2-one

A. D,L-Bromosuccinic acid mono-4-nitrobenzyl ester

D,L-Bromosuccinic acid was allowed to react with TFAA in following the procedure and conditions described by Example 3A to prepare D,L-bromosuccinic anhydride represented by the formula

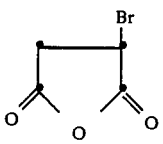

IR (neat): 1780 cm$^{-1}$, 1870 cm$^{-1}$

NMR (CDDl₃)δ 2.85–4.04 (m, 2H), 4.84–5.05 (dd, 1H).

The bromoanhydride was allowed to react in dry THF with 4-nitrobenzyl alcohol to provide in 97% yield an 80:20 ratio of the D- L-bromosuccinic acid mono-4-nitrobenzyl esters.

B. O-Methyl D,L-bromosuccinic acid hydroxamate mono-4-nitrobenzyl ester

The bromosuccinic acid ester (Part A) was reacted with methoxyamine hydrochloride by following the procedures described in the preceding examples (Part C) to provide the O-methyl hydroxamate mono ester melting at about 104°–107° C.

Percent Elemental Analysis calculated for $C_{11}H_{13}BrN_2O_6$:

Theory: C, 39.89; H, 3.60; N, 7.76; Br, 22.16 Found: C, 40.09; H, 3.59; N, 7.57; Br, 22.34.

IR (KBr): 1730 cm$^{-1}$, 1660 cm$^{-1}$.

NMR (CDCl₃)δ 3.16–3.42 (m, 2H), 3.78 (s, 3H), 3.8–4.3 (m, 1H), 5.25 (s, 2H), 7.3–8.3 (m, 4H).

C. D,L-1-Methoxy-4-(4-nitrobenzyloxycarbonyl)azetidin-2-one

O-Methyl D,L-bromosuccinic acid hydroxamate mono ester (Part B) was cyclized to the azetidin-2-one in anhydrous DMF/CH₂Cl₂ (1:1, v:v) with sodium hydride. D,L-1-Methoxy-4-(4-nitrobenzyloxycarbonyl)azetidin-2one melting at about 65° to about 68° C. was obtained in 31% yield.

IR (CHCl₃): 1785 cm$^{-1}$, 1750 cm$^{-1}$.

NMR (CDCl₃):δ 2.87–3.05 (m, 2H), 3.87 (s, 3H), 4.55–4.68 (dd, 1H), 7.5–8.4 (m, 4H), 5.37 (s, 2H).

MS (CI with methane) m/e 281 (M+1).

EXAMPLE 7

D-1-Pivalyloxy-4-(benzyloxycarbonyl)azetidin-2-one

D-Malic acid monobenzyl ester prepared as described by Example 1A was allowed to react with pivalyloxyamine hydrochloride according to the method described in the preceding examples (Part B) to provide in 89% yield O-pivalyloxy-D-malic acid hydroxyamate monobenzyl ester melting at about 75° to about 76° C.

IR (KBr): 1780 cm$^{-1}$, 1730–35 cm$^{-1}$, 1690 cm$^{-1}$,

NMR (CDCl₃):δ 1.3 (s, 9H), 2.7–2.8 (s, 2H), 4.42–4.7 (t, 1H), 5.25 (s, 2H),.7.4 (s, 5H), 9.1 (br., 2H, NH, OH).

The O-pivalyloxy hydroxamate monoester was cyclized to the azetidin-2-one by following the procedures described in the preceding Examples 1-3 (Part C) to provide the azetidine-2-one represented by the formula

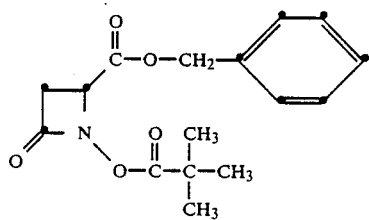

The product melted at about 47° to about 49.5° C. and was obtained in 93% yield.

$[α]_D^{20}$= +61.6° (C=2, methanol).

IR (KBr): 1810–1815 cm$^{-1}$, 1770 cm$^{-1}$, 1745 cm$^{-1}$

NMR (CDCl₃): δ 1.22 (s, 9H), 3.01–3.12 (dd, 2H), 4.47–4.61 (dd, 1H), 5.18 (s, 2H), 7.35 (s, 5H).

Percent Elemental Analysis calculated for $C_{16}H_{19}NO_5$: Theory: C, 62.95; H, 6.23; N, 4.39

Found: C, 62 88, H, 6.16; N, 4.36.

EXAMPLE 8

D-1-Methoxy-4-(benzyloxycarbonyl)azetidin-2-one

D-Malic acid monobenzyl ester prepared as described by Example 1A was reacted with methoxyamine hydrochloride according to the method of the preceding examples (Part B) to provide in yields varying from 73% to 100% O-methyl D-malic acid hydroxamate monobenzyl IR (neat): 1750 cm$^{-1}$, 1680 cm$^{-1}$.

NMR (CDCl₃):δ 2.5–2.8 (br. s, 2H), 3.6 (s, 3H), 4.4–4.7 (t, 1H), 5.16 (s, 2H), 7.3 (s, 5H), 9.1 (br. H, OH, NH).

Percent Elemental Analysis calculated for $C_{12}H_{15}NO_5$: Theory: C, 56.91; H, 5.93; N, 5.53 Found: C, 57.17; H, 5.75; N, 55.74.

The O-methyl hydroxamate monoester was cyclized in 75% yield to the azetidin-2-one represented by the formula

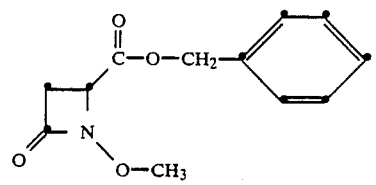

IR (neat): 1800 cm$^{-1}$, 1750 cm$^{-1}$

NMR (CDCl₃): δ 2.75–2.85 (m, 2H), 3.78 (s, 3H), 4.3–4.42 (dd, 1H), 5.23 (s, 2H), 7.37 (s, 5H)

MS (CI with methane) m/e 236 (M+1).

EXAMPLE 9

D-1-Pivalyloxymethoxy-4-(methoxycarbonyl)-azetidin-2-one

D-Malic acid monomethyl ester, prepared as described by Example 2A, was allowed to react with pivalyloxymethoxyamine hydrochloride by following the procedures and conditions described by the preceding examples (Part B) to provide as an oil N-(t-butyloxycarbonylmethoxy) D-malic acid hydroxamate monomethyl ester.

NMR (CDCl₃):δ 1.48 (s, 9H), 2.7 (br m, 2H), 3.8 (s, 3H), 4.35 (s, 2H), 4.6 (m, 1H), 9.0 (br, NH, OH).

MS (CI with methane) m/e 278 (M+1).

The hydroxamate monoester was cyclized to the azetidin-2-one represented by the formula

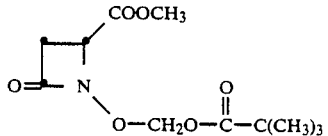

The azetidin-2-one was obtained as an oil in 93% yield.

NMR (CDCl₃): δ 1.47 (s, 9H), 2.9 (dd, 2H), 3.8 (s, 3H), 4.45 (s, 2H), 4.5 (m, 1H).

EXAMPLE 10

1-Pivalyloxy-4-(benzyloxycarbonylmethyl)-azetidin-2-one

β-Hydroxyglutaric acid was converted to the monobenzyl ester by the method described by Example 1A for the preparation of D-malic acid monobenzyl ester, and the monoester was reacted at pH 4.5 with O-pivaloylhydroxylamine hydrochloride and N-ethyl-N'-(3-dimethylaminopropyl)carbodiimide. The product, O-pivaloxyl-β-hydroxyglutaric acid hydroxamate monobenzyl ester, melted at about 71° to about 73° C.

IR (CHCl$_3$) 1710 cm$^{-1}$, 1770 cm$^{-1}$.

NMR (CDCl$_3$): δ 1.28 (s, 9H), 2.50 (d, 2H), 2.65 (d, 2H), 4.48 (m, 1H), 5.2 (s, 2H), 7.37 (s, 5H), 9.78 (bs, 2H, NH and OH).

Elemental Analysis (percent) calculated for C$_{17}$H$_{23}$NO$_6$:

Theory: C, 60.52; H, 6.87; N, 4.15 Found: C, 60.65; H, 6.74; N, 4.22.

The O-pivaloyl hydroxamate benzyl ester was cyclized by reaction in dry acetonitrile with triphenylphosphine (2 equiv.), carbontetrachloride (5 equiv.) and triethylamine (1 equiv.). The β-lactam product, -pivaloyloxy-4-(benzyloxycarbonylmethyl)azetidin-2-one, was purified by chromatography over silica gel.

NMR (CDCl$_3$, 90 MHz): δ 1.23 (s, 9H), 2.8 (m, 4H), 4.43 (dq, 1H), 5.13 (s, 2H), 7.4 (s, 5H).

IR (CHCl$_3$) 1805 cm$^{-1}$, 1775 cm$^{-1}$, 1730 cm$^{-1}$.

EXAMPLE 11

1-Benzyloxy-4-(methoxycarbonylmethyl)azetin-2-one

In following the method described by Example 10, monomethyl β-hydroxyglutaric acid is reacted with O-benzylhydroxylamine hydrochloride and a water soluble diimide to provide O-benzyl β-hydroxyglutaric acid hydroxamate methyl ester. The hydroxamate is cyclized with triphenylphosphine and DEAD under anhydrous conditions to provide the product represented by the formula

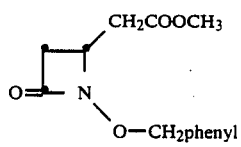

EXAMPLE 12

1-Benzyloxy-3-ethyl-4-(methoxycarbonyl)-azetidin-2-one

A. Alkylation of diisopropyl malate (ethylmalic acid)

To a stirred solution of diisopropylamine (19.69 ml., 140 mmole) in 200 ml. of dry THF maintained under nitrogen at 0° C. was added with stirring n-butyl lithium (86.68 ml., 134.37 mmole). After 10 minutes the solution was cooled to about −50° C. and a solution of diisopropyl malate (13.95 g., 63.99 mmole) prepared with D-malic acid in dry hexamethylphosphoramide, HMPA (11.45 ml., 63.99 mmole) was added. The resulting red solution was allowed to warm to a temperature of about −10° C., and after a few minutes the mixture was cooled to about −20° C. and ethyl iodide (6.14 ml., 76.88 mmole) was added. The reaction mixture was allowed to warm to room temperature over one hour and was then heated for 45 minutes at 45° C. The reaction mixture was allowed to cool to room temperature, was neutralized with 1M citric acid, and extracted with ethyl acetate. The extract was washed with brine, dried over magnesium sulfate, filtered, and evaporated to dryness to yield 15.5 g. (62.99 mmole, 98.5% yield) of diisopropyl ethylmalate as an oil. The product was obtained as a mixture of the diastereoisomers represented by the following formulas

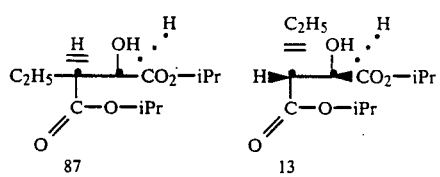

IR (neat): 3500 cm$^{-1}$ (OH), 1730 cm$^{-1}$ (ester) NMR (90 MHz, CDCl$_3$, diastereoisomeric mixture) 1.03 (t, 3H), 1.26 (d, J=5.5 Hz, 6H), 1.33 (d, J =5.5 Hz, 6H), 1.86 (m, 2H), 2.83 (m, 1H), 4.37 (d, J=Hz, 1H), 5.23 (m, 2H).

B. Ethylmalic acid monomethyl ester

The diisopropyl ethylmalate (diastereoisomeric mixture) prepared as described above is saponified in aqueous dioxane with potassium hydroxide at the reflux temperature. The diacid is recovered by passing the cooled reaction mixture over Dowex resin (sulfonic acid form) and evaporating the eluate.

The diacid (ethylmalic acid) was converted (via the procedure described by Example 3A) to the monomethyl ester represented by the formula

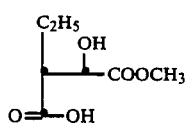

by first reacting the diacid with TFAA to obtain the ethylmalic anhydride trifluoroacetate represented by the formula

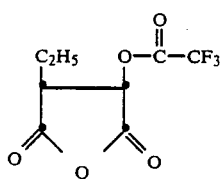

The anhydride is then reacted with methyl alcohol to obtain the monomethyl ester of the above formula.

C. O-Benzyl ethylmalic acid hydroxamate methyl ester

The monomethyl ester (Part B) is reacted in aqueous THF (pH 4.5–5.0) with O-benzylhydroxylamine hydrochloride and 3 equivalents of a water soluble carbodiimide, and the O-benzyl hydroxamate methyl ester recovered from the aqueous reaction mixture by extraction with ethyl acetate.

The hydroxamate monomethyl ester is cyclized to the azetidin-2-one represented by the formula

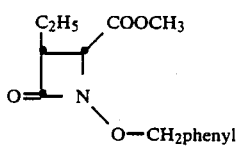

by the method described by Example 1C.

EXAMPLE 13

1-Benzyloxy-3-ethyl-4-(methoxycarbonyl)-azetidin-2-one (via alkylation of diethylmalate)

A. Diethyl ethylmalate

Diethyl malate was alkylated with ethyl iodide by following the alkylation method described by Example 12A to provide in 84% yield diethyl ethylmalate as an oil. The product was obtained as a mixture (87:13) of the diastereoisomers represented by the formulas

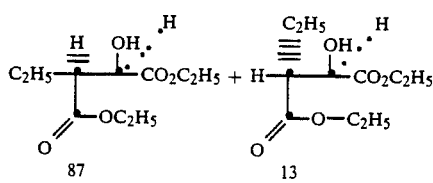

IR (neat): 3500 cm⁻¹ (OH), 1730 cm⁻¹.

NMR (90 MHz, CDCl₃): δ 1.0 (t, 3H, J=6Hz), 1.26 (m, 6H), 1.76 (m, 2H), 2.78 (m, 1H), 4.03-4.4 (m, 5H).

B. Ethylmalic acid

To a solution of the diastereoisomeric ethyl esters (Part A) (5.9 g., 27 mmole) in 20 ml. of dioxane was added a 20% solution of potassium hydroxide (13.7 ml.). Next, a 1:1 mixture of dioxane:water was added until a homogeneous reaction mixture was obtained. The mixture was then heated at the reflux temperature for 16 hours. The reaction mixture was cooled and passed through 50 g. of Dowex resin (SO₃H phase) and the eluate evaporated. The semi-solid residue was triturated with diethyl ether and cooled to yield a white solid. The white solid was filtered, washed with 1:1 diethyl ether:-hexane and dried in a vacuum desiccator to yield 2.02 g. (46% yield) of the diastereoisomer represented by the formula A.

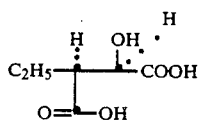

MS (CI with methane) m/e 219 (M+1), 145 (—CO₂C₂H₅).

NMR (90 MHz, DMSOd6): δ 0.85 (t, 3H), 1.42 (m, 2H), 2.50 (m, 1H), 4.12 (d, 1H, J=5Hz), 7.5 (broad OH, CO₂H).

The ethereal solution obtained by filtering the above triturate was evaporated to provide 2.3 g. (52.5% yield) of a mixture of two diasterioisomers, one of which was the isomer A (above) first isolated.

C. Ethylmalic acid monomethyl ester

The diacid (diasterioisomer A) was converted to the monomethyl ester by the procedure described by Example 13B. The monomethyl ester of the formula was obtained as an oil in 87% yield.

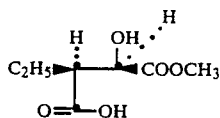

IR (neat) 3100-3550 cm⁻¹, 1740 cm⁻¹.

NMR (90 MHz, CDCl₃) δ 1.0 (t, 3H), 1.8 (m, 2H), 2.83 (m, 1H), 3.80 (s, 3H), 4.36 (d, 1H, J=4.5 Hz), 7.56 (broad OH and CO₂H).

MS m/e 175, 159, 117.

D. O-Benzyl ethylmalic acid hydroxamate monomethyl ester

The monomethyl ester B (above) (3.111 g., 17.7 mmole) was dissolved in 30 ml. of THF-H₂O (1:1) and the pH of the solution adjusted to 4.5. To the solution was added a solution (pH 4.5) of O-benzylhydroxylamine hydrochloride (3.4 g., 21.2 mmole) in 15 ml. of water. A solution of 3 equivalents of N-ethyl-N'-(3-dimethylaminopropyl)carbodiimide in 10 ml. of water was next added, and the pH of the mixture was maintained between about 4.5 and about 5.0 while the mixture was stirred for 10 minutes. The reaction mixture was extracted with ethyl acetate and the extract was washed twice with 20 ml. portions of 1M citric acid, once with 20 ml. of brine, and dried over magnesium sulfate. The drying agent was filtered and the filtrate evaporated to yield the product as an oil. The oil solidified on standing to yield 4.5 g. (91% yield) of the O-benzyl hydroxamate methyl ester. The NMR spectrum of the crude product showed a trace of a succinimide side product plus the desired product.

The product was recrystallized from ethyl acetate-hexane to give white needles melting at about 104° to about 105° C.

IR (CHCl₃) 3400 cm⁻¹, 1740 cm⁻¹, 1680 cm⁻¹.

NMR (90 MHz, CDCl₃) δ 0.93 (t, 3H, J=6.5 Hz), 1.71 (m, 2H), 2.46 (broad m, 1H), 3.75 (s, 3H), 4.26 (d, 1H, J=5.5 Hz), 4.87 (s, 2H), 7.42 (s, 5H), 8.90 (broad NH).

MS (CI with methane) m/e 282 (M+1).

E. 1-Benzyloxy-3-ethyl-4-(methoxycarbonyl)azetidin-2-one

The O-benzylhydroxamate methyl ester (Part D) was cyclized to the β-lactam represented by the formula

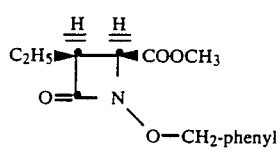

by the method described in the previous Examples. A 75% yield of the β-lactam as a solid was obtained.

IR (CHCl₃) 1725 cm⁻¹, 1780 cm⁻¹.

NMR (300 MHz, CDCl₃) δ 0.959 (t, J=7.5 Hz, 3H), 1.567 (m, 2H), 3.056 (q, 1H, 2 superimposed triplets), 3.76 (s, 3H), 4.2-(d, J=6 HZ, 1H), 5.054 and 5.076 (each s, 2H, NHOCH₂phenyl), 7.400 (m, 5H).

MS (CI with methane) m/e 264 (m+1).

EXAMPLE 14

1-Benzyloxy-3-amino-4-(methoxycarbonyl)azetidin-2-one

A. Malic acid monobenzyl monomethyl ester

Malic acid monomethyl ester (Example 2A) was dissolved in DMF and one equivalent of O-benzyl-N,N'-diisopropylisourea was added. The reaction mixture was stirred at room temperature for about 17 hours. Methylene chloride was added to the mixture and the suspension was filtered to remove the diisopropylurea. The filtrate was further diluted with methylene chloride and washed with water, 10% aqueous sodium carbonate, water, and with brine and was dried over magnesium sulfate. After filtration and evaporation the monobenzyl monomethyl ester was obtained as an oil.

NMR (90 MHz, CDCl₃) δ 2.85 (d, 2H), 3.6 (d, OH, br.), 3.7 (s, 3H), 4.5 (apparent q, 1H), 5.12 (s, 2H), 7.35 (s, 5H).

B. 2-Azidomalic acid monobenzyl monomethyl ester

The diester (Part A, 238 mg., 1 mmole) was dissolved in 10 ml. of THF and the solution cooled to −78° C. under nitrogen. In a separate flask, diisopropylamine (0.35 ml., 2.49 mmole) was dissolved in 5 ml. of THF and the solution cooled to 0° C. under nitrogen. To this latter solution were added 1.85 ml. of 1.3M butyllithium (ca. 2.4 mmole) in hexane, and the solution was stirred at 0° C. for 5 minutes and then added to the malic acid diester solution at −78° C. After the light yellow solution was stirred for 15 minutes, 200 mg. (ca. 1 mmole) of tosyl azide in 3 ml. of THF were added. The yellow reaction mixture was stirred at −78° C. for one hour and then allowed to warm to room temperature over 30 minutes. Trimethylchlorosilane (0.46 ml., 3.56 mmole) was added to the brownish reaction mixture and the mixture was stirred at room temperature for one hour.

The reaction mixture was concentrated by evaporation to a volume of about 5 ml. and the concentrate added to 40 ml. of methylene chloride. The solution was washed twice with 20 ml. portions of 10% aqueous sodium bicarbonate, 20 ml. of water, and with 20 ml. of brine and was dried, filtered and evaporated to yield the crude product as a yellow-brown oil.

The oil was chromatographed on silica gel with methylene chloride-hexane via gradient elution to provide as an oil 128 mg. (46% yield) of a mixture of diasteroisomers represented by the formulas

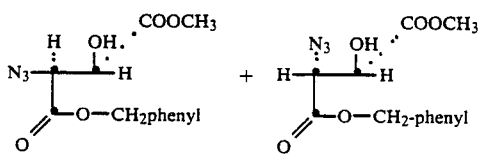

IR (neat): 2100 cm⁻¹ (N₃), 1750-1760 cm⁻¹ (broad ester).

NMR (90 MHz, CDCl₃) δ 3.57 and 3.75 (s, s, OCH₃ of 2 diastereomers), 4.1 and 4.2 (d,d from 2 diestereomers, 1H), 4.6 and 4.8 (d, d, from 2 diastereomers, 1H), 5.17 and 5.22 (s, s, from 2 diastereomers, 2H), 7.35 and 7.4 (s, s, from 2 diastereomers, 5H).

MS (CI with methane) m/e 178 (M⁺ −91, loss of benzyl).

C. O-Benzyl-3-aminomalic acid hydroxamate monomethyl ester

The 2-azidomalic acid monobenzyl monomethyl ester (Part B) is hydrogenated in THF under 50 psi hydrogen pressure over 5% palladium on carbon catalyst, the catalyst was filtered and the filtrate evaporated to provide crude 3-amino malic acid monomethyl ester represented by the formula

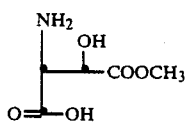

The amino ester is purified via an acid-base wash in diethyl ether or methylene chloride.

The amino ester is converted to the O-benzyl hydroxamate with O-benzylhydroxylamine hydrochloride by the method described in the preceding Examples.

EXAMPLE 15

1-Benzyloxy-3-(t-butyloxycarbonylamino)-4-methoxycarbonylazetidin-2-one

To a solution of 0.482 ml. (7.98 g.) of thionyl chloride in 30 ml. of methyl alcohol was added at room temperature in solid form 1 g. (6.71 mmole) of D,L-threo-β-hydroxyaspartic acid and the solution was heated at the reflux temperature for 3 hours. After cooling, the reaction mixture was evaporated to a white semi-solid residue containing in a 4:1 ratio ('HNMR) the desired monoester to the diester as the hydrochloride salts.

The crude mono methyl ester hydrochloride salt (ca. 5 mmole) was dissolved in 30 ml. of aqueous THF (1:1, v:v) and 1.31 g. (6 mmole) of di-tert-butyldicarbonate were added followed by 1.66 ml. (ca. 12 mmole) of triethylamine. The suspension obtained was stirred at room temperature for 2 hours after which a negative ninhydrin test was obtained with an aliquot of the reaction mixture. The reaction mixture was poured into a mixture of 25 ml. of ethyl acetate and 20 ml. of 5% aqueous sodium bicarbonate. The aqueous layer was separated and extracted twice with 20 ml. portions of ethyl acetate. The aqueous layer was then acidified to pH 4 with solid citric acid, and then to pH 2 with cold 6N hydrochloric acid. The acidified aqueous layer was extracted with three 25 ml. portions of ethyl acetate and the extracts combined, washed with brine, dried over magnesium sulfate, filtered and evaporated to a residual oil (83.5% crude) of product represented by the formula

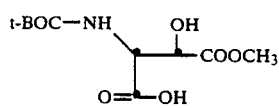

NMR (90 MHz, CDCl₃) δ 1.42 (s, 9H), 3.8 (s, 3H), 4.8 (m, 2H), 5.7 (broad d, NH), 7.3-8 (broad, OH, CO₂H).

Mass Spect. (CI with CH₄) m/e 264 (M+1).

The protected amino monomethyl ester obtained as described above (263 mg., 1 mmole) was added to a solution of 300 mg. (1.88 mmole) of O-benzylhydroxylamine hydrochloride in 20 ml. of water at pH 4.5 (adjusted with 1N sodium hydroxide). To the solution was added a solution of 500 mg. (ca. 2.6 mmole) of N-ethyl-N'-(dimethylaminopropyl)carbodiimide in 3 ml. of water. A precipitate began forming immediately and the pH of the mixture drifted to 5.5. The pH was readjusted to 4.5 with 1.2N hydrochloric acid and after 20 minutes the white solid precipitate was separated by filtration and air dried to yield 347 mg. (94% yield) of the O-benzylhydroxamate represented by the formula

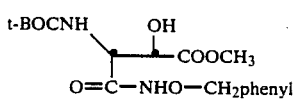

The product was recrystallized from ethyl acetate-hexane to yield 347 mg. (84%) melted at about 132° to about 133.5° C.

NMR (90 MHz, CDCl₃) δ 1.38 (s, 9H), 3.75 (s, 3H), 3.75 (broad s, OH), 4.6 (m, 2H), 4.9 (s, 2H), 5.6 (d, NH), 7.4 (s, 5H), 9.55 (broad s, NH).

The O-benzylhydroxamate monomethyl ester (250 mg., 0.679 mmole) was dissolved in 10 ml. of dry THF containing triphenylphosphine (180 mg., 0.68 mmole) maintained under a drying tube. Diethyl diazodicarboxylate (0.11 ml., 0.7 mmole) was added and the reaction solution was stirred at room temperature for 3 hours. The solution was then evaporated to dryness and the residue was chromatographed on silica gel with methylene chloride:isopropyl alcohol (99.5:0.5, v:v). Fractions containing β-lactam were combined and evaporated to dryness to yield 160 mg. (67% yield) of product as an oil. After recrystallization from ethyl acetate-hexane the product was obtained as a white solid melting at about 93.5° to about 95° C.

NMR (90 MHz, CDCl₃) δ 1.4 (s, 9H), 3.75 (s, 3H), 4.23 (d, 1H, J=2.5), 4.43 (d, broad, J=7-8), 5.05 (s, 2H), 5.65 (d, broad, NH, J=7-8), 7.4 (m, 5H).

IR (neat oil before recrystallization): 1800 cm⁻¹, 1755 cm⁻¹, 1715 cm⁻¹.

EXAMPLE 16

1-Benzyloxy-3-amino-4-methoxycarbonylazetidin-2-one

The 3-(tert-butyloxycarbonylamino) substituted β-lactam prepared as described by Example 15 is deprotected by treating the protected amino β-lactam ester with trifluoroacetic acid. The product represented by the following formula is obtained as the trifluoroacetate salt.

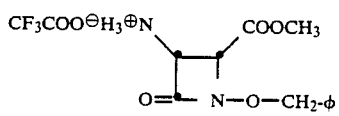

EXAMPLE 17

1-Benzyloxy-4-aminomethylazetidin-2-one

γ-Amino-β-hydroxybutyric acid was reacted with carbobenzoxy chloride to yield the N-carbobenzoxy derivative.

The N-carbobenzoxy derivative was reacted with O-benzylhydroxylamine and dicyclohexylcarbodiimide to provide the hydroxamate represented by the formula

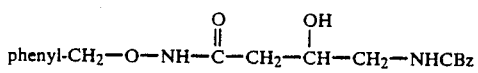

wherein CBz=carbobenzoxy.

The hydroxamate was obtained in 68% yield and melted at about 120.5° to about 122° C. NMR (60 MHz, CDCl₃): δ 2.3 (m, 2H), 3.2 (m, 2H), 4.0 (m, 1H), 4.8 (s, 2H), 5.1 (s, 2H), 7.33 (s, 5H), 7.38 (s, 5H).

The hydroxamate was cyclized to the azetidinone using diethyl azodicarboxylate and triphenylphosphine by the procedures described herein. The product, 1-benzyloxy-4-(N-carbobenzoxy)aminomethylazetidin-2-one, melted at about 86° to about 87° C.

Elemental Analysis calculated for C₁₉H₂₀N₂O₄: Theory: C, 67.05; H, 5.92; N, 8.23;
Found: C, 66.89; H, 6.13; N, 8.47.

NMR (60 MHz, CDCl₃) δ 2.5 (m, 2H), 3.1-3.4 (m, 2H), 3.6 (m, 1H), 4.9 (s, 2H), 5.1 (s, 2H), 5.5 (br t, NH), 7.33 (s, 5H), 7.7 (s, 5H).

IR (CHCl₃) 1770 cm⁻¹, 1710 cm⁻¹.

EXAMPLE 18

1-Benzyloxy-4-hydroxymethylazetidin-2-one

To a solution of 311 mg. (1 mmole) of 1-benzyloxy-4-benzyloxycarbonylazetidin-2-one in 10 ml. of tetrahydrofuran, cooled in an ice bath, was added a solution of 37 mg. of sodium borohydride in 3 ml. of water. The solution was stirred at ice bath temperature for one hour and was then poured into a separatory funnel containing 25 ml. of ethyl acetate, 25 ml. of water and 2 ml. of acetic acid. After shaking, the layers were separated and the aqueous layer was extracted twice with 25 ml. portions of ethyl acetate. These two extracts were combined with the organic layer. The organic layer was washed twice with 15 ml. portions of 5% aqueous sodium bicarbonate and 15 ml. of brine and was dried over sodium sulfate, filtered and evaporated to give the product as a crude oil. The oil was chromatographed on silica gel with gradient elution (30% ethyl acetate −70% hexanes to 100% ethyl acetate) The fraction containing the purified product (Rf=0.15, silica gel thin layer in 1:1 ethyl acetate-hexanes) was evaporated to yield 121 mg. (61% yield) of the product as an oil.

IR (neat): 1760 cm⁻¹.

NMR (60 MHz, CDCl₃): δ 2.5-2.65 (m, 3H), 3.55-3.65 (broad, 3H), 4.9 (s, 2H), 7.4 (s, 5H).

EXAMPLE 19

1-Benzyloxy-4-iodomethylazetidin-2-one

To a solution of 786 mg. (3.97 mmole) of 1-benzyloxy-4-hydroxymethylazetidin-2-one in 30 ml. of THF were added 7.49 mmole of dicyclohexylcarbodiimide methiodide and the mixture was heated at 40° to 50° C. under nitrogen for 48 hours. The reaction mixture was evaporated and the residue was chromatographed in silica gel using methylene chloride-hexanes for elution. The 4-iodomethyl product was obtained as an oil in 62.6% yield.

IR (neat): 1775 cm⁻¹.

MS m/e 317.

NMR (60 MHz, CDCl₃) δ 2.5 (d, 1H, J=4 Hz), 2.72 (d, 1H, J=10 Hz), 3.1 (t, 2H), 3.63 (m, 1H), 5.0 (s, 2H), 7.43 (s, 5H).

EXAMPLE 20

1-Benzyloxy-4-(2-hydroxyethyl)azetidin-2-one

1-Benzyloxy-4-(benzyloxycarbonylmethyl)azetidin-2-one is reacted with trimethylsilyliodide under anhydrous conditions to provide the 2-carboxymethyl deesterified product and the latter is esterified with pentachlorophenol. The ester is reduced with sodium borohydride to the 2-hydroxyethyl title compound.

EXAMPLE 21

1-Benzyloxy-4-(2-iodoethyl)azetidin-2-one is obtained by reacting the corresponding 4-(2-hydroxyethyl)azetidin-2-one with dicyclohexylcarbodiimide methiodide.

EXAMPLE 22

1-Benzyloxy-4-(carboxymethyl)azetidin-2-one is obtained by the hydrogenolysis of 1-benzyloxy-4-(ben-

EXAMPLE 23

1-Benzyloxy-3-(t-butyloxycarbamido)-4-formylazetidine-2-one is prepared by reacting 1-benzyloxy-3-(t-butyloxycarbamido)-4-(2-hydroxyethyl)azetidin-2-one with Jones' reagent (chromium trioxide-H₂SO₄) in acetone.

EXAMPLE 24

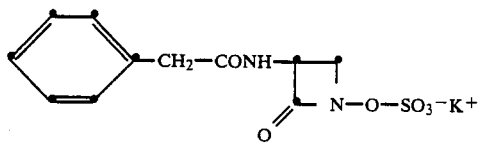

1-Hydroxy-3β-phenylacetylaminoazetidin-2-one, 100 mg., was added to a solution of 79.5 mg. (ca. 0.5 mmole) of pyridine.SO₃ complex (Aldrich Chemical Co.) in 2 ml. of dry pyridine. The reaction mixture was stirred at room temperature under a drying tube. The pyridine.SO complex was all dissolved within 2-3 minutes. Thin layer chromatography (silica gel, ethyl acetate-5% acetic acid) run on aliquots of the mixture taken at 0.5 hours and 1 hour showed some starting material (Rf=0.25) and two other spots (Rf 0.05-0.1 and 0.0). After 2 hours the TLC was the same and 30 mg. of additional pyridine.SO₃ complex were added to the reaction mixture. Five minutes after the addition the TLC showed only a trace of the starting material. The reaction mixture was stirred at room temperature for two more hours and was then evaporated under 0.2 mm of Hg. at room temperature. The residue (glass) was dissolved in the minimum amount of water and applied to a 2×20 cm. column of DOWEX (K⁺ form). The product was eluted with water and 20 ml. fractions collected. Fraction 2, with strong absorption in the UV at 254 nm., was lyophilized to yield 171 mg. of the product as a white powder contaminated with a little inorganic salt.

NMR (D₂O, D₆ acetone ca. 2:1): unlocked spectrum with H₂O peak at 4.85 δ and all peaks listed relative to the H₂O peak: 3.75 (s, 2H), 3.9 (dd, H), 4.25 (t, 1H), 4.85 (s, H₂O), 5.05 (dd, 1H), and 7.65 (s, 5H) δ.

The product when tested in the disc-plate assay showed zones of inhibition against *Staphylococcus aureus, Sarcina lutea*, Salmonella, *Escherichia coli*, and Pseudomonas.

EXAMPLE 25

By following the procedures described by Example 24, 1-hydroxy-3β-[2-(2-tritylaminothiazol-4-yl)-2-methoxyimino]acetamido-4-methylazetidin-2-one is reacted in pyridine with pyridine.SO₃ complex to form the compound represented by the following formula

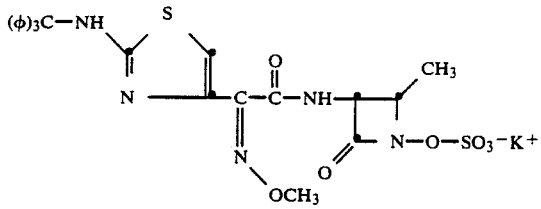

The trityl protecting group is removed with trifluoroacetic acid to provide the free aminothiazole compound.

EXAMPLE 26

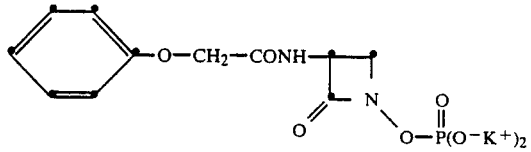

1-Hydroxy-3β-phenoxyacetylaminoazetidin-2-one is reacted in acetonitrile with diphenyl chlorophosphate in the presence of 1 equivalent of pyridine to form the azetidinyl diphenylphosphate. The latter is then subjected to hydrogenolysis over PtO₂ catalyst in tetrahydrofuran under 50 psi of hydrogen pressure to provide the mono azetidinyl ester diacid. The latter is converted to the title compound as the dipotassium salt over DOWEX (K⁺ form).

EXAMPLE 27 syn 1-(Carboxymethoxy)-3-[2-(2-aminothiazol-4-yl)-2-methoxyiminoacetamido]-2-azetidinone potassium salt To a solution of 1.0 g. (4.24 mmole, 1 eg.) of 1-hydroxy-3-benzyloxycarbonylamino-2-azetidinone in 50 ml. of 1:1, v:v tetrahydrofuran:water were added at room temperature 580 mg. (4.24 mmole, 1 eg.) of potassium carbonate along with 1.01 g (4.24 mmole, 1 eg.) of the 2-trimethylsilylethyl ester of bromoacetic acid. The reaction mixture was stirred at room temperature and was monitored by thin layer chromatography (ethyl acetate:hexanes, 70:30, v:v, silica). After 3 hours the reaction mixture was dissolved in ethyl acetate and the solution washed with aqueous 5% sodium bicarbonate and brine, dried over magnesium sulfate, filtered, evaporated, and chromatographed over silica gel. There were obtained 1.40 g of the 2-trimethylsilylethyl ester of 1-(carboxymethoxy)-3-benzyloxycarbonylamino-2-azetidinone as a thick clear oil.

IR (neat): 1785 cm⁻¹ and 1720 cm⁻¹.

NMR (CDCl₃) 7.55 (s, 5H), 6.50 (d, 1H), 5.15 (s, 2H), 4.6 (m, 1H), 4.5 (s, 2H), 4.3 (t, 2H), 3.9 (t, 1H), 3.65 (m, 1H), 0.9 (t, 2H), 0.0 (s, 9H) delta.

The 2-trimethylsilylethyl ester prepared as described above (55 mg., 0.139 mmole, 1 eg) was dissolved in 15 ml. of absolute ethyl alcohol and 0.116 ml. of 1.2N hydrochloric acid (0.139 mmole, 1 eq.) was dissolved in 15 ml. of absolute ethyl alcohol and 0.116 ml. of 1.2N hydrochloric acid (0.139 mole, 1 eq.) was added to the solution along with 5% palladium-on-carbon catalyst. Hydrogen was passed over the top of the stirred solution at room temperature for 45 minutes. The reduction was followed by thin-layer chromatography (ethyl acetate:hexanes, 70:30, v:v, silica). The catalyst was separated by filtration and the filtrate was evaporated to dryness. There were obtained 41 mg. of the 2-trimethylsilylethyl ester of 1-(carboxymethoxy)-3-amino-2-azetidinone hydrochloride salt as a clear oil.

To a cold (0° C.) solution of 42 mg. (0.142 mmole, 1 eq.) of the 3-amino-2-azetidinone ester hydrochloride salt obtained as described above in 15 ml. of 1:1, tetrahydrofuran:water was added with stirring 0.0395 ml. of triethylamine (0.284 mmole, 2 eq.). Next, 45 mg. (0.142 mmole, 1 eq.) of the N-hydroxybenztriazole (HBT)

ester of 2-(2-aminothiazol-4-yl)-2-methoxyiminoacetic acid were added. The ice bath was removed and the reaction mixture was stirred for 24 hours. The reaction solution was dissolved in ethyl acetate and the solution washed with aqueous 5% sodium bicarbonate and brine, and was dried over magnesium sulfate, filtered and chromatographed over silica. There were obtained 48 mg. of the acylated product, the 2-trimethylsilylethyl ester of 1-(carboxymethoxy)-3-[2-(2-aminothiazol-4-yl)-2-methoxyiminoacetamido]-2-azetidinone, as an oil.

IR (CDCl$_3$): 1780 cm$^{-1}$, 1750 cm$^{-1}$, 1665 cm$^{-1}$.

NMR (CDCl$_3$): 8.9 (d, 1H), 6.9 (s, 1H), 6.0 (br s, 2H), 5.3 (m, 1H), 4.7 (s, 2H), 4.35 (t, 2H), 4.25 (t, 1H), 4.1 (s, 3H), 3.9 (dd, 1H), 1.0 (t, 2H), 0.0 (s, 9H).

The aminothiazole ester was deesterified as follows. To a solution of 63 mg. (0.142 mmole, 1 eq.) of the ester in 10 ml. of tetrahydrofuran was added with stirring 0.141 ml. (0.142 mmole, 1 eq.) of 1N tetrabutylammonium fluoride. The reaction mixture was stirred at room temperature for 4 hours. Thin layer chromatography (ethyl acetate:acetic acid:water, 15:3:1, silica) showed starting material remained. The reaction mixture was evaporated to an oily residue and the oil containing the carboxylic acid product was dissolved in water. The aqueous solution was washed with ethyl acetate to remove starting material. The washed aqueous solution containing the deesterified acid was then passed through a column packed with Dowex (K$^+$). The collected fractions were combined and evaporated to dryness. There were obtained 50 mg. of the title compound as a yellow solid (93% yield).

IR (KBr): 1760 cm$^{-1}$.

nmr (D$_2$O): 7.1 (s, 1H), 5.0 (m, 1H), 4.45 (s, 2H), 4.1 (t, 1H), 4.0 (s, 3H), 3.9 (dd, 1H) delta.

EXAMPLE 28 syn
1-(Carboxymethoxy)-3β-[2-(2-aminothiazol-4-yl)-2-methoxyiminoacetamido]-4α-methyl-2-azetidinone potassium salt By following the procedures and reaction conditions and by using the reagents employed in the preparation described in Example 27, 1-hydroxy-3β-benzyloxycarbonylamino-4α-methyl-2-azetidinone was alkylated with the 2-trimethylsilylethyl ester of bromoacetic acid to obtain the 2-trimethylsilylethyl ester of 1-(carboxymethoxy)-3β-benzyloxycarbonylamino-4α-methyl-2-azetidinone. The amino-protected ester was hydrogenated in the presence of one equivalent of hydrochloric acid to provide 1-(carboxymethoxy)-3β-amino-4α-methyl-2-azetidinone 2-trimethylsilylethyl ester as the hydrochloride salt. The 3-amino azetidinone ester was N-acylated with the active HBT ester of 2-(2-aminothiazol-4-yl)-2-methoxyiminoacetic acid to provide 1-(carboxymethoxy)-3β-[2-(2-aminothiazol-4-yl)-2-methoxyiminoacetamido]-4α-methyl-2-azetidinone 2-trimethylsilylethyl ester. The latter product was deesterified with tetrabutylammonium fluoride and the free acid converted to the potassium salt with Dowex (K$^+$).

IR (KBr): 1770 cm$^{-1}$.

NMR (D$_2$O) 7.15 (s, 1H), 4.6 (m, 1H), 4.55 (s, 2H), 4.3 (m, 1H), 4.05 (s, 3H), 1.5 (d, 3H) delta.

EXAMPLE 29

1-(Carboxymethoxy)-3β-phenylacetylamino-2-acetidinone

To a solution of 59 mg. (0.27 mmole) of 1-hydroxy-3β-phenylacetylamino-2-azetidinone in 3 ml of tetrahydrofuran and 4 ml. of water were added 37 mg. (1 eq.) of potassium carbonate and 61 mg. (1 eq.) of benzyl bromoacetate. The reaction was stirred at room temperature for 2.75 hours and monitored via tlc (ethyl acetate:hexanes, 50:50, silica). Then the reaction mixture was poured into 50 ml. of ethyl acetate and the mixture was washed with aqueous 5% sodium bicarbonate. The layers were separated and the aqueous phase was washed with ethyl acetate. The ethyl acetate layer and washes were combined and washed with brine, dried over magnesium sulfate, filtered, and evaporated to provide the reaction product mixture containing the product (benzyl ester of title compound), benzyl alcohol, and benzyl bromoacetate. The mixture was chromatographed over silica to yield 35 mg. of the product, 1-(benzyloxycarbonylmethoxy)-3β-phenylacetylamino-2-azetidinone (35% yield).

NMR (CDCl$_3$) 7.4 (s, 5H), 7.3 (s, 5H), 7.5 (br d, 1H), 4.6 (m, 1H), 4.5 (s, 2H), 3.9 (t, 1H), 3.5 (br s, 3H) delta.

The product obtained as described above, 90 mg., was dissolved in 50 ml. of tetrahydrofuran and 10% palladium on carbon catalyst was added to the solution. The suspension was stirred at room temperature while hydrogen was passed over the solution. After 30 minutes tlc (70:30, ethyl acetate:hexanes, silica) showed the absence of starting ester. The catalyst was filtered and the filtrate was evaporated to dryness yielding a white solid residue melting at about 110° C. to 115° C. The residue was crystallized from a mixture of acetone and hexanes to yield 48 mg. of the title compound melting at about 108° C. to 110° C.

IR (KBr): 2900 cm$^{-1}$ to 3700 cm$^{-1}$ broad peak and 1770 cm$^{-1}$ β-lactam carbonyl.

NMR (d$_6$-acetone) 8.1 (d, 1H), 7.4 (s, 5H), 6.8 (br s, 1H), 4.8 (m, 1H), 4.54 (s, 2H), 3.9 (t, 1H), 3.4 (m, 1H), 3.5 (s, 1H) delta.

Mass spec. M+1 279.

EXAMPLE 30

1-(Carboxymethoxy)-3β-phenylacetylamino)-4α-methyl-2-azetidinone sodium salt

1-Threonine methyl ester (8.3 g., 62.4 mmole) was dissolved in 100 ml of a saturated solution of sodium bicarbonate in water and the solution was cooled in an ice bath. To the cold solution were added 8.9 ml. (6.25 mmole) of benzyl chloroformate and triethylamine (1 eq.). After 30 minutes the ice bath was removed and the solution was stirred for 5 hours at room temperature. The solution was then extracted with ethyl acetate and the extract washed with 1.2N hydrochloric acid, water, and brine, dried over magnesium sulfate and evaporated to dryness. The residue was crystallized from a mixture of ethyl acetate and hexanes to yield 5.5 g. (33% yield) of N-carbobenzoxy 1-threonine methyl ester melting at about 88° C. to 90° C.

The N-Cbz$^2$-1-threonine methyl ester, 5.0 g. (18.7 mmole) was dissolved in 75 ml of dry methyl alcohol and the solution was cooled in an ice bath. To the cold solution was added a freshly-prepared solution of hydroxylamine (2 eq.) in methyl alcohol and the formation of the hydroxamic acid was followed by tlc (ethyl acetate, silica). After 45 minutes all of the starting material had reacted and 6.5 ml. (2 eq.) of acetic anhydride were added to the mixture. The reaction mixture containing the O-acetylhydroxamate was poured into a mixture of ethyl acetate and 5% aqueous sodium bicarbonate.

After shaking, the layers were separated and the ethyl acetate layer was washed with 5% aqueous sodium bicarbonate. The aqueous layer and the wash were combined and acidified with 6N hydrochloric acid and extracted with methylene chloride. The extract was washed with brine, dried over magnesium sulfate, and evaporated to dryness. The solid residue was crystallized from a mixture of ethyl acetate and hexanes to yield 4.11 g (71% yield) of the N-Cbz-1-threonine O-acetylhydroxamate as a white solid melting at about 118° C. to 120° C.

IR (KBr): 3250 cm$^{-1}$, 1800 cm$^{-1}$, 1660 cm$^{-1}$.

NMR (CDCl$_3$) 10.3 (br s, 1H), 7.3 (s, 5H), 5.9 (br d, 1H) 5.2 (s, 2H), 4.3 (br d, 2H), 3.4 (br s, 1H), 2.1 (s, 3H), 1.2 (d, 3H) delta.

The N-Cbz$^2$-1-threonine O-acetylhydroxamate (1 g., 3.2 mmole) was dissolved in 25 ml. of dry acetonitrile, 2 ml. of carbon tetrachloride were added, and while the solution was stirred at room temperature 0.448 ml (3.2 mmole) of triethylamine and 0.845 g. (3.2 mmole) of triphenylphosphine were added. After 3 hours the reaction mixture was evaporated and the residue dissolved in ethyl acetate. The solution was washed with water, brine, dried and evaporated. The residue was chromatographed over silica to provide 790 mg. (84% yield) 1-acetoxy-3-benzyloxycarbonylamino-4-methyl-2-azetidinone.

IR, (KBr): 3325 cm$^{-1}$, 1810 cm$^{-1}$, 1780 $-^1$1720 cm$^{-1}$.

NMR (CDCl$_3$) 7.3 (s, 5H), 6.0 (br s, 1H), 5.1 (s, 2H), 4.3 (d, 1H), 4.0 (m, 1H), 2.1 (s, 3H), 1.4 (d, 3H) delta.

The 1-acetoxy-β-lactam (775 mg., 2.65 mmole) was dissolved in 50 ml. ethyl acetate and 808 mg. (3.2 mmole, 1.2 eq.) of phenylacetic acid anhydride and 5% palladium on carbon catalyst were added to the solution. Hydrogen was passed over the solution with stirring for 24 hours. The reduction mixture was filtered to remove catalyst and the filtrate was washed with aqueous 5% sodium bicarbonate and brine, dried, evaporated and chromatographed over silica to provide 180 mg. (25% yield) of 1-acetoxy-3β-phenylacetylamino-4α-methyl-2-azetidinone.

IR (KBr): 3350 cm$^{-1}$, 1810 cm$^{-1}$, 1780 cm$^{-1}$.

NMR (CDCl$_3$) 7.3 (s, 5H), 4.4 (dd, 1H), 3.9 (m, 1H), 3.5 (s, 2H), 2.1 (s, 3H), 1.4 (d, 3H).

The 1-acetoxy-3-phenylacetylamino-4-methyl-2-azetidinone, 180 mg. (0.65 mmole) was dissolved in 6 ml. of dry methyl alcohol and 3 ml. of water were added. The solution was cooled to about 0° C. in an ice bath and 176 mg. (1.63 mmole, 2.5 eq.) of sodium carbonate were added with stirring. After 35 minutes the hydrolysis mixture was added to aqueous 5% sodium bicarbonate and the solution extracted with ethyl acetate. The extract was washed with brine, dried and evaporated to give 106 mg. (70% yield) of 1-hydroxy-3β-phenylacetylamino-4α-methyl-2-azetidinone.

IR (KBr): 1760 cm$^{-1}$.

NMR (d$_6$ acetone): 8.2 (br d, 1H), 7.4 (s, 5H), 4.3 (dd, 1H), 3.8 (m, 1H), 3.5 (s, 2H), 1.2 (d, 3H).

The 1-hydroxy β-lactam, 106 mg. (0.453 mmole), was dissolved in 10 ml. of tetrahydrofuran and 103 mg. (0.453 mmole, 1 eq.) of benzyl bromoacetate and a solution of 62 mg. (0.453 mmole) of potassium carbonate in 10 ml. of water were added to the solution. The solution was stirred at room temperature for 2.5 hours and was then dissolved in ethyl acetate. The solution was washed with aqueous 5% sodium bicarbonate, and brine, evaporated, and chromatographed over silica to give 90 mg. (52% yield) of 1-(benzyloxycarbonylmethoxy)-3β-phenylacetylamino-4α-methyl-2-azetidinone as an oil.

NMR (CDCl$_3$) 7.35 (s, 5H), 7.25 (s, 5H), 6.9 (d, 1H), 5.15 (s, 2H), 4.5 (s, 2H), 4.15 (dd, 1H), 3.75 (dd, 1H), 3.5 (s, 2H), 1.4 (d, 3H) delta.

The benzyl ester obtained above, 90 mg. (0.235 mmole), was dissolved in 25 ml. of tetrahydrofuran and 10% palladium on carbon catalyst was added. Hydrogen was passed over the suspension for 30 minutes, the catalyst filtered, and the filtrate evaporated to remove the solvent. The product, 1-(carboxymethoxy)-3β-phenylacetylamino-4α-methyl-2-azetidinone, was obtained an oil.

NMR (d$_6$-acetone): 7.7 to 9.0 (br s, 1H), 8.1 (d, 1H), 7.4 (s, 5H), 4.5 (s, 2H), 4.2 (d, 1H), 3.9 (m, 1H), 3.5 (s, 2H), 1.3 (d, 3H) delta.

The oil was passed through a Dowex (Na$^+$) column with water and the effluent evaporated to give 40 mg. (54% yield) of the title compound.

EXAMPLE 31

1-[(1-Benzyltetrazol-5-yl)methoxy]-3β-phenylacetylamino-2-azetidinone

To a solution of 104 mg (0.472 mmol) of 1-hydroxy-3β-phenylacetylamino-2-azetidinone in 15 ml. of 1:1, v:v, THF:water were added with stirring 65 mg. (0.472 mmole) of potassium carbonate and 98 mg. (0.472 mmole) of 5-chloromethyl-1-benzyltetrazole. After stirring at room temperature for 2 hours tlc (70:30, ethyl acetate:hexanes, silica) indicated the presence of only starting material. A few crystals of sodium iodide were added to catalyze the reaction. After stirring for 24 hours the reaction mixture was taken up in ethyl acetate and the solution was washed with aqueous 5% sodium bicarbonate and brine, dried, evaporated, and chromatographed over silica. There were obtained 55 mg. (33%) of the title compound as an oil.

NMR (CDCl$_3$) 7.4 (d, 10H), 7.2 (br d, 1H), 5.75 (s, 2H), 5.1 (s, 2H), 4.6 (m, 1H), 3.7 (t, 1H), 3.5 (m, 3H).

IR (KBr) 1780 cm$^{-1}$.

The 1-benzyl group of the 1-benzyltetrazole compound is removed, e.g. by hydrogenolysis over Pd on carbon to provide the 1H-tetrazole compound. The latter may be converted to the salt form of the tetrazole with a suitable base such as sodium or potassium hydroxide.

I claim:

1. A compound of the formula

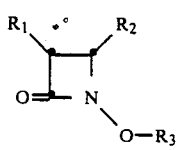

wherein R$_1$ is C$_1$-C$_4$ alkyl; R$_2$ is carboxy, protected carboxy, C$_1$-C$_4$ alkyl substituted by carboxy, protected carboxy or hydroxy; and R$_3$ is benzyl, methoxybenzyl, nitrobenzyl, diphenylmethyl or pivaloyl.

2. A compound of the formula

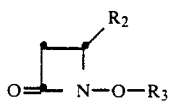

wherein $R_2$ is carboxy, protected carboxy, $C_1$–$C_4$ alkyl substituted by carboxy, protected carboxy, hydroxy, halogen, amino or protected amino; and $R_3$ is benzyl, $C_1$–$C_4$ alkyl, pivaloyl or t-butyloxycarbonylmethyl.

3. The compound of claim 2 wherein $R_2$ is protected carboxy, or carboxy.

4. The compound of claim 3 of the formula

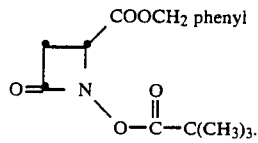

5. The compound of claim 3 of the formula

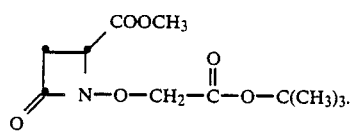

6. The compound of claim 1 of the formula

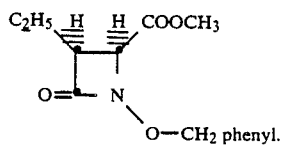

7. The compound of claim 1 of the formula

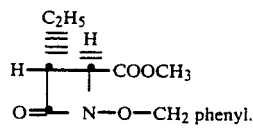

8. The compound of claim 2 wherein $R_2$ is $C_1$–$C_4$ alkyl substituted by hydroxy.

9. The compound of claim 8 of the formula

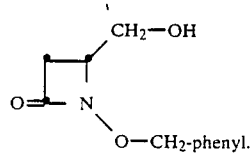

10. The compound of claim 2 wherein $R_2$ is $C_1$–$C_4$ alkyl substituted by halogen.

11. The compound of claim 10 of the formula

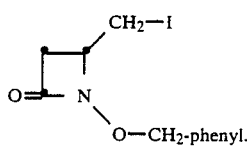

12. The compound of claim 2 wherein $R_2$ is $C_1$–$C_4$ alkyl substituted by amino or protected amino.

13. The compound of claim 12 of the formula

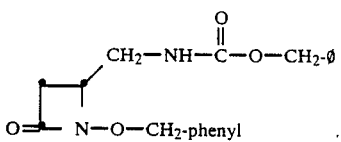

14. The compound of claim 12 of the formula

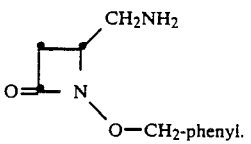

15. The compound of claim 2 wherein $R_2$ is $C_1$–$C_4$ alkyl substituted by carboxy, or protected carboxy.

16. The compound of claim 15 of the formula

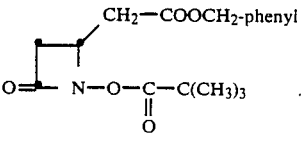

* * * * *